US006080398A

United States Patent [19]
Pelus et al.

[11] Patent Number: 6,080,398
[45] Date of Patent: *Jun. 27, 2000

[54] TRUNCATED GRO AND KC CHEMOKINES HAVING ENHANCED BIOACTIVITY

[75] Inventors: Louis Martin Pelus, Richboro; Pradip Kumar Bhatnagar, Exton; Andrew Garrison King, Blue Bell; Joanna Maria Balcarek, Bala Cynwyd, all of Pa.

[73] Assignee: SmithKline Beecham Corporation, Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/557,142

[22] PCT Filed: Jun. 3, 1994

[86] PCT No.: PCT/US94/06264

§ 371 Date: Mar. 5, 1996

§ 102(e) Date: Mar. 5, 1996

[87] PCT Pub. No.: WO94/29341

PCT Pub. Date: Dec. 22, 1994

Related U.S. Application Data

[63] Continuation of application No. 08/073,800, Jun. 8, 1993, abandoned.

[51] Int. Cl.$^7$ .......................... A61K 38/19; C07K 14/52; C12N 15/19

[52] U.S. Cl. .......................... 424/85.1; 530/350; 530/351; 536/23.5; 435/69.5; 435/69.1; 435/320.1; 435/325; 435/252.3; 435/254.11

[58] Field of Search .................................... 530/350, 351; 424/85.1; 514/2; 536/23.5; 435/320.1, 325, 252.3, 254.11, 69.1, 69.5

[56] References Cited

U.S. PATENT DOCUMENTS

| | | | |
|---|---|---|---|
| 5,154,921 | 10/1992 | Sager et al. | 424/93.7 |
| 5,459,128 | 10/1995 | Rollins et al. | 514/8 |
| 5,703,206 | 12/1997 | Wolpe . | |
| 5,739,103 | 4/1998 | Rollins et al. | 514/8 |
| 5,854,412 | 12/1998 | Rollins et al. | 536/23.1 |

FOREIGN PATENT DOCUMENTS

| | | |
|---|---|---|
| WO 91/07988 | 6/1991 | WIPO . |
| WO 92/00327 | 1/1992 | WIPO . |
| WO 92/01039 | 1/1992 | WIPO . |
| WO 92/06196 | 4/1992 | WIPO . |
| WO 94/28916 | 12/1994 | WIPO . |
| WO 96/19234 | 6/1996 | WIPO . |

OTHER PUBLICATIONS

Proost, et al., "Identification of Novel Granulocyte Chemotactic Protein (GCP–2) from Human Tumor Cells", (1993), Journal of Immunology, vol. 150:3, pp. 1000–1010.

Cuenca, et al, "Characterization of GRO α, β, and γ expression in human colonic tumours: potential significance of cytokine involvement", (1992), Surgical Oncology, vol. 1, pp. 323–329.

Broxmeyer, et al., "Comparative Analysis of the Human Macrophage Inflammatory Protein Family of Cytokines (Chemokines) on Proliferation of Human Myeloid Progenitor Cells", (1993), Journal of Immunology, vol. 150:8, pp. 3448–3458.

Broxmeyer, et al., "Enhancing and Suppressing Effects of Recombinant Murine Macrophage Inflammatory Proteins on Colony Formation In Vitro by Bone Marrow Myeloid Progenitor Cells", (1990), Blood, vol. 76:6, pp. 1110–1116.

Bowie, et al., "Deciphering the Message in ProteinSequences: Tolerance to Amino Acid Substitutions", (1990), Science, vol. 247, pp. 1306–1310.

Watanabe, et al., "Rat Gro/Melanoma Growth–Stimulating Activity. Assessment of the Structure Responsible for Chemotactic Activity by Use of Its Fragments Prepared by Proteolysis and Chemical Synthesis", (1992), Cytokine, vol. 4:1, pp. 12–17.

Lord, et al., "Macrophage inflammatory protein: its characteristics, biological properties and role in the regulation of haemopoiesis", (1993), Intl. Journal of Hematology, vol. 57, pp. 197–206.

Sager, R., "Gro as a Cytokine", (1990), Prog. Leukocyte Biol., vol. 10 A, Oppenheim, J.J., et al., eds., Mol. Cell. Biol. of Cytokines (Proc. 2d Int'l Workshop on Cytokines, Dec. 10–14, 1989), pp. 327–332.

Wolpe, et al., "Macrophage inflammatory proteins 1 and 2: members of a novel superfamily of cytokines", (1989), The FASEB Journal, vol. 3, pp. 2565–2573.

Anisowicz, et al., "Constitutive overexpression of a growth–regulated gene in transformed Chinese hamster and human cells", (1987), Proc. Natl. Acad., vol. 84, pp. 7188–7192.

Richmond, et al., "Molecular characterization and chromosomal mapping of melanoma growth stimulatory activity, a growth factor structurally related to β–thromboglobulin", (1988), The EMBO Journal, vol. 7:7, pp. 2025–2033.

M.Y. Stoeckle, "Post–transcriptional regulation of groα, β, γ, and IL–8 mRNAs by IL–1β", (1991), Nucleic Acids Research, vol. 19, No. 4, pp. 917–920.

Sporn, et al., "Isolation of Adherence Specific cDNA Clones from a Monocyte cDNA Library", (1988), J. Leukocyte Biology, 44(4), p. 267.

Sporn, et al., "Monocyte Adherence Induces Novel Genes Sharing Homology With Mediators of Inflammation and Tissue Repair", (1989), J. Leukocyte Biology, 46(4), p. 328.

Sporn, et al., "Monocyte Adherence Results in Selective Induction of Novel Genes Sharing Homology With Mediators of Inflammation and Tissue Repair", (1990), J. Immunology, 144(11), pp. 4434–4441.

(List continued on next page.)

Primary Examiner—David L. Fitzgerald
Attorney, Agent, or Firm—Linda E. Hall; Stephen A. Venetianer; Charles M. Kinzig

[57] ABSTRACT

The present invention provides method of increasing the biological activity of KC, gro-α, gro-β, and gro-γ proteins, truncated and modified proteins characterized by having biological activity at least 1 log better than the full-length protein, and pharmaceutical compositions containing same.

54 Claims, 6 Drawing Sheets

OTHER PUBLICATIONS

Haskill, et al., "Identification of three related human GRO genes encoding cytokine functions", (1990), *Proc. Natl. Acad. Sci. USA*, 87(19), pp. 7732–7736.

Anisowicz, et al, "Functional diversity of gro gene expression in human fibroblasts and mammary epithelial cells", (1988), *Proc. Natl. Acad. Sci. USA*, 87(19), pp. 9645–9649.

Trask, et al., "The Gro Gene as Growth Factor and Cytokine", (1990), *J. Cell Biochem.*, Suppl. 0 (14 pt. B) p. 5.

Tekamp–Olson, et al., "Cloning and Characterization of cDNAs for Murine Macrophage Inflammatory Protein 2 and its Human Homologues", (1990), *J. Exp. Med.*, 172, pp. 911–919.

Suggs, et al., "Use of synthetic oligonucleotides as hybridization probes: Isolation of cloned cDNA sequences for human $\beta 2$–microglobulin", (1981), *Proc. Natl. Acad. Sci. USA*, 78:11, pp. 6613–6617.

E. Brandt, et al., "A Novel Molecular variant of the Neutrophil–Activating Peptide NAP-2 With Enhanced Biological Activity is Truncated at the C–Terminus: Identification By Antibodies With Defined Epitope Specificty", (1993), *Molecular Immunology*, vol. 30:11, pp. 979–991.

B. Moser, et al., "Interleukin–8 Antagonists Generated by N–Terminal Modification", (1993), *Journal of Biological Chemistry*, vol. 268:10, pp. 7125–7128.

C.A. Hérbert, et al., "Endothelial and Leukocyte Forms of IL–8", (1990), *Journal of Immunology*, vol. 145:9, pp. 3033–3040.

J. Van Damme, "The neutrophil–activating proteins inteleukin 8 and $\beta$–thromboglobulin: in vitro and in vivo comparison of $NH_2$–terminally processed forms", (1990), *European Journal of Immunology*, vol. 20, pp. 2113–2118.

A.M. Gronenborn, et al., "Modeling, the three–dimensional structure of the moncyte chemo–attractant and activating protein MCAF/MCP–1 on the basis of the solution structure of inteleukin–8", (1991), *Protein Engineering*, vol. 4;3, pp. 263–269.

J.J. Oppenheim, et al., "Properties of the Novel Proinflammatory Supergene "Intercrine" Cytokine Family", *Annual Review of Immunology*, vol. 9, pp. 617–648.

S. Nourshargh, et al., "A Comparative Study of the Neutrophil Stimulatory Activity In Vitro and Pro–Inflammatory Properties In Vivo of 72 Amino Acid and 77 Amino Acid IL–8", (1992), *Journal of Immunology*, vol. 148:1, pp. 106–111.

I. Clark–Lewis, et al., "Structure–Activity Relationships of Interleukin–8 Determined Using Chemically Synthesized Analogs", (1991), *Journal of Biological Chemistry*, vol. 266:34, pp. 23128–23134.

| | | | | | | | | | |
|---|---|---|---|---|---|---|---|---|---|
| 5' Ala | Pro | Ile | Ala | Asn | Glu | Leu | Arg | Cys | Gln | 10 |
| Cys | Leu | Gln | Thr | Met | Ala | Gly | Ile | His | Leu | 20 |
| Lys | Asn | Ile | Gln | Ser | Leu | Lys | Val | Leu | Pro | 30 |
| Ser | Gly | Pro | His | Cys | Thr | Gln | Thr | Glu | Val | 40 |
| Ile | Ala | Thr | Leu | Lys | Asn | Gly | Arg | Glu | Ala | 50 |
| Cys | Leu | Asp | Pro | Glu | Ala | Pro | Leu | Val | Gln | 60 |
| Lys | Ile | Val | Gln | Lys | Met | Leu | Lys | Gly | Val | 70 |
| Pro | Lys | | | | | | | | | 72 |

FIG. 1

| | | | | | | | | | |
|---|---|---|---|---|---|---|---|---|---|
| 5' Ala | Ser | Val | Ala | Thr | Glu | Leu | Arg | Cys | Gln | 10 |
| Cys | Leu | Gln | Thr | Leu | Gln | Gly | Ile | His | Pro | 20 |
| Lys | Asn | Ile | Gln | Ser | Val | Asn | Val | Lys | Ser | 30 |
| Pro | Gly | Pro | His | Cys | Ala | Gln | Thr | Glu | Val | 40 |
| Ile | Ala | Thr | Leu | Lys | Asn | Gly | Arg | Lys | Ala | 50 |
| Cys | Leu | Asn | Pro | Ala | Ser | Pro | Ile | Val | Lys | 60 |
| Lys | Ile | Ile | Glu | Lys | Met | Leu | Asn | Ser | Asp | 70 |
| Lys | Ser | Asn | | | | | | | | 73 |

FIG. 2

| | | | | | | | | | |
|---|---|---|---|---|---|---|---|---|---|
| 5' Ala | Pro | Leu | Ala | Thr | Glu | Leu | Arg | Cys | Gln | 10 |
| Cys | Leu | Gln | Thr | Leu | Gln | Gly | Ile | His | Leu | 20 |
| Lys | Asn | Ile | Gln | Ser | Val | Lys | Val | Lys | Ser | 30 |
| Pro | Gly | Pro | His | Cys | Ala | Gln | Thr | Glu | Val | 40 |
| Ile | Ala | Thr | Leu | Lys | Asn | Gly | Gln | Lys | Ala | 50 |
| Cys | Leu | Asn | Pro | Ala | Ser | Pro | Met | Val | Lys | 60 |
| Lys | Ile | Ile | Glu | Lys | Met | Leu | Lys | Asn | Gly | 70 |
| Lys | Ser | Asn | | | | | | | | 73 |

FIG. 3

| | | | | | | | | | |
|---|---|---|---|---|---|---|---|---|---|
| 5' Ala | Ser | Val | Val | Thr | Glu | Leu | Arg | Cys | Gln | 10 |
| Cys | Leu | Gln | Thr | Leu | Gln | Gly | Ile | His | Leu | 20 |
| Lys | Asn | Ile | Gln | Ser | Val | Asn | Val | Arg | Ser | 30 |
| Pro | Gly | Pro | His | Cys | Ala | Gln | Thr | Glu | Val | 40 |
| Ile | Ala | Thr | Leu | Lys | Asn | Gly | Lys | Lys | Ala | 50 |
| Cys | Leu | Asn | Pro | Ala | Ser | Pro | Met | Val | Gln | 60 |
| Lys | Ile | Ile | Glu | Lys | Ile | Leu | Asn | Lys | Gly | 70 |
| Ser | Thr | Asn | | | | | | | | 73 |

FIG. 4

TRUNCATED GRO AND KC CHEMOKINES HAVING ENHANCED BIOACTIVITY

This application is a national stage (35 U.S.C. § 371) of international application Ser. No. PCT/US94/06264, which is in turn a continuation of application Ser. No. 08/073,800, filed Jun. 8, 1993, now abandoned.

FIELD OF THE INVENTION

The present invention relates generally to certain proteins and to methods of improving the biological activity of certain proteins, and more specifically, chemokines.

BACKGROUND OF THE INVENTION

All the members of the intercrine or chemokine family are basic heparin-binding polypeptides which have four cysteine residues which form two disulfide bridges. All these proteins which have been functionally characterized appear to be involved in proinflammatory and/or restorative functions. As such, these molecules are anticipated to have therapeutic potential in bone marrow transplantation and the treatment of infections, cancer, myelopoietic dysfunction, graft versus host disease, and autoimmune diseases.

The chemokine family can be divided into two subfamilies depending upon their amino acid sequence and chromosomal location. The members of the α subfamily are termed the "C-X-C" subfamily because the first two cysteines are separated by only one amino acid. The human genes in this subfamily include IL-8, GRO/MGSA, and IP-10; murine counterparts include KC and macrophage inflammatory protein 2 (MIP-2). In the chemokine β subfamily, the first two cysteines are in an adjacent position (the "C-C" subfamily). This subfamily includes human MCAF, LD-78, ACT-2, and RANTES. The murine counterparts are JE, TCA-3, MIP-1α, and MIP-1β [J. J. Oppenheim et al, *Annu. Rev. Immunol.*, 9:617–648 (1991)].

The murine KC gene product [Oquendo et al, *J. Biol. Chem.*, 264:4233 (1989)] is induced by platelet-derived growth factor (PDGF) and this is thought to be the murine homolog of the human MGSA/groα gene (63.0% amino acid identity to mMIP-2). KC has been expressed in COS-1 cells to show that it encodes a secreted protein [Oquendo, cited above].

Two forms of MIP have been found in cultures of macrophage tumor cells from the mouse: MIP-1 and MIP-2. Murine MIP-2 (mMIP-2) is an inducible protein whose cDNA also has been cloned and sequenced [International Patent Application, Publication No. WO 90/02762 (Mar. 22, 1990)]. Murine MIP-2 has been shown to have potent chemotactic activity for human polymorphonuclear leukocytes (PMN), and to induce PMN degranulation of lysozyme but not of β-glucuronidase [Wolpe et al, *J. Exp. Med.*, 167:570 (1987)]. Further, mMIP-2 has been shown to have myelopoietic enhancing activities for CFU-GM [Broxmeyer et al, *J. Exp. Med.*, 170:1583 (1989)]. The human counterpart of this factor was found to consist of two species, MIP-2α and MIP-2β, also termed gro-β and gro-γ, respectively.

The cDNA and amino acid sequences of human gro-β are provided in International Patent Application, Publication No. WO 92/00327 (Jan. 9, 1992); the cDNA and amino acid sequences of human gro-γ are provided in International Patent Application, Publication No. WO 92/00326 (Jan. 9, 1992). Each of these sequences were predicted to encode a 73 amino acid mature protein.

MGSA or gro-α [Richmond et al, *EMBO J.*, 7:2025 (1988)] is an autocrine growth factor with potent mitogenic activity secreted by human melanoma cells and is the product of the human gro gene [Anisowicz et al, *Proc. Natl. Acad. Sci.*, 84:7188 (1987)].

There remains a need in the art for methods of enhancing the bioactivity of these mature proteins to enable their efficient use as therapeutic or pharmaceutical products, and to minimize the amounts of the proteins necessary to produce a therapeutic effect, thereby lowering toxicity.

SUMMARY OF THE INVENTION

In one aspect, the present invention provides a modified chemokine, which includes KC protein, human gro α, gro-β, and gro-γ, which modified protein is characterized by truncation of between about 2 to about 8 amino acids at the amino terminus of the mature protein and by at least a log higher biological activity than the mature protein.

In another aspect, the present invention provides a modified chemokine which is characterized by truncation of between about 2 to about 10 amino acids at the carboxy terminus of the mature protein and by at least a log higher biological activity than the mature protein.

In still another aspect, the present invention provides a multimeric protein which comprises an association of two or more modified proteins of this invention. These multimers preferably contain multiple copies of the same modified protein, e.g., a dimer of truncated KC protein. However, multimeric forms of two or more different modified proteins of this invention are also included in this invention. Multimeric forms of a modified protein of this invention and another known mature protein are also encompassed by this invention.

In a further aspect, the present invention provides a method of enhancing the biological activity of chemokines by modifying and/or truncating the proteins as described above.

In yet another aspect, the present invention provides pharmaceutical and diagnostic compositions containing the modified and multimeric proteins of the invention, as well as methods for administering same in therapeutic treatments.

In a further aspect, the present invention provides antibodies characterized by the ability to selectively bind the modified chemokines of the invention.

In still another aspect, the present invention provides a method of monitoring the effect of a selected hematopoiesis stimulating agent upon hematopoietic synergistic factor (HSF) in vivo through use of an antibody of the invention.

In yet another aspect, the present invention provides a method of inducing HSF in vivo by administering (pGlu-Glu-Asp)$_2$-Sub-(Lys)$_2$ [SEQ ID NO: 5].

Other aspects and advantages of the present invention are described further in the following detailed description of the preferred embodiments thereof.

BRIEF DESCRIPTION OF THE DRAWINGS

FIG. 1 provides the published amino acid sequence [SEQ ID NO: 1] of the mature, native murine KC protein.

FIG. 2 provides the published amino acid sequence [SEQ ID NO: 2] of the mature, gro-alpha human protein.

FIG. 3 provides the published amino acid sequence [SEQ ID NO: 3] of the mature, human gro-β protein.

FIG. 4 provides the published amino acid sequence [SEQ ID NO: 4] of the mature, human gro-γ protein.

DETAILED DESCRIPTION OF THE INVENTION

Figure 5:
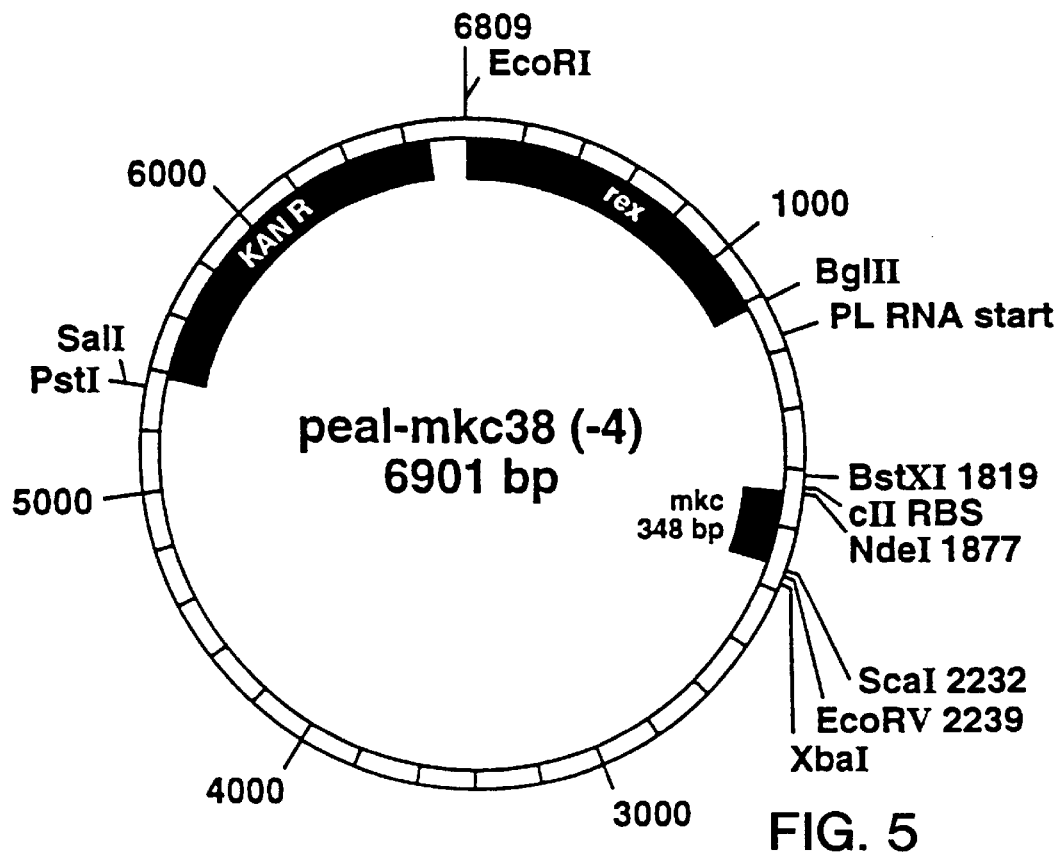
FIG. 5 is a DNA map of the plasmid pea1-mkc38(−4), which is described below in Example 2.

The present invention provides modified proteins, specifically chemokines, associated with inflammatory responses, hematopoiesis and myelopoiesis, which modified proteins are characterized by having enhanced biological activity as compared to the corresponding unmodified or untruncated mature native proteins.

As defined herein, "hematopoietic synergistic factor" or "HSF" refers to a class of proteins, including the naturally occurring chemokines and the modified chemokines of the invention, which are characterized by having synergistic activity in stimulating hematopoiesis when administered in vivo and in vitro with another hematopoietic factor, such as a colony stimulating factor (see Example 8), or combined with naturally circulating CSFs. The term "chemokines", also known as "intercrines" include, among others, the proteins conventionally referred to in the art as KC protein, gro-β, gro-α, and gro-γ, all of mammalian origin. The amino acid sequences of four of the mature chemokines [SEQ ID NOS: 1–4] identified above are illustrated in FIGS. 1 through 4 herein. Also included by this definition are analogs or derivatives of these proteins which share the biological activity of the mature protein.

As defined herein, such analogs and derivatives include modified proteins also characterized by alterations made in the known amino sequence of mature proteins, e.g., the proteins provided in SEQ ID NOS: 1–4. Such analogs are characterized by having an amino acid sequence differing from that of the mature protein by 8 or fewer amino acid residues, and preferably by about 5 or fewer residues. It may be preferred that any differences in the amino acid sequences of the proteins involve only conservative amino acid substitutions. Conservative amino acid substitutions occur when an amino acid has substantially the same charge as the amino acid for which it is substituted and the substitution has no significant effect on the local conformation of the protein or its biological activity. Alternatively, changes such as the elimination or introduction of a certain amino acid in the sequence which may alter the stability of the protein, or permit it to be expressed in a desired host cell may be preferred.

As used herein, "enhanced biological activity" refers to biological activity which is at least one log higher, i.e. 10 times or 10 fold, than that observed in the full-length mature protein in the HSF assay of Example 8. Additionally, this term refers to biological activities not characteristic of the mature protein, e.g., as with KC, the full-length mature protein may be inactive, while the modified protein has significant activity.

The present invention provides modified desamino chemokines. The term "desamino" is used to indicate chemokines or proteins of the invention which have been modified such that between about 2 to about 8, and preferably from about 5 to about 8, amino acids have been removed from the amino terminus of the mature protein. Optionally, particularly when expressed recombinantly, the desamino chemokines of the invention may optionally contain an inserted N-terminal Met. During expression by the host cell, this optional Met may be cleaved. Alternatively, if so desired, this amino acid may be cleaved through enzyme digestion or other known means.

In one embodiment of this aspect, the present invention provides a desamino KC protein, which is characterized by having a truncated amino (or N) terminus in comparison to the mature KC protein. The modified protein can be truncated at a position between amino acid residues #2 through 8 of mature KC protein of FIG. 1 [SEQ ID NO: 1]. Preferably, this desamino KC, contains amino acids 5–72 of the mature KC protein of SEQ ID NO: 1; i.e., the first four amino acid residues of the amino terminus of the illustrated KC protein are missing in this protein.

Surprisingly, the inventors have discovered that this desamino KC is characterized by having bioactivity in a hemopoietic synergistic factor assay (see Example 8) of at least $10^{14}$ Units/mg in contrast to the unmodified, full-length mature KC [SEQ ID NO: 1] which is inactive (−0 Units/mg). It is anticipated that when purified, this modified chemokine will be characterized by an even higher bioactivity. The construction, synthesis and assay of the desamino KC are described in detail in the examples below.

Another modified chemokine embodied by the present invention is a desamino gro-β (also known as MIP-2α) protein. This protein comprises the amino acid sequence of mature gro-β protein truncated at its N terminus between amino acid positions 2 and 8 of FIG. 3 [SEQ ID NO: 3]. In a preferred embodiment, the desamino protein of the invention has a protein sequence spanning amino acids 5 to 73 of the mature gro-β of SEQ ID NO: 3.

The inventors have surprisingly discovered that this desamino-gro-β is characterized by having at least about two logs higher biological activity than unmodified, full-length human gro-β.

Another embodiment of the present invention is a desamino gro-γ (also known as MIP-2β) protein. This protein comprises the amino acid sequence of mature gro-γ protein truncated at its N terminus between amino acid positions 2 and 8 of SEQ ID NO: 4. In a preferred embodiment, the modified protein of the invention has a protein sequence spanning amino acids 5 to 73 of the mature gro-γ [SEQ ID NO: 4]. The inventors have discovered that this desamino gro-γ has at least 2 log greater bioactivity in the assay of Example 8 than the full-length mature gro-γ. It is anticipated, that upon further purification, an even greater bioactivity will be observed.

Another modified protein embodied by the present invention is a desamino gro-α protein (also known as MGSA). This protein comprises the amino acid sequence of mature gro-α protein truncated at its N terminus between amino acid positions 2 and 8 of FIG. 2 [SEQ ID NO: 2]. In a preferred embodiment, the modified protein of the invention has a protein sequence spanning amino acids 5 to 73 of the mature gro-α of SEQ ID NO: 2. Upon modification, an increase in activity similar to that observed with these other gro proteins is anticipated for desamino gro-α.

The present invention also provides modified descarboxy chemokines or other proteins. Such a descarboxy chemokine comprises a full length mature chemokine having about 2 to about 10 amino acids deleted from its carboxy terminus. Optionally, the N-terminal methionine which is optionally inserted into the protein for expression purposes, may be cleaved, either during the processing of the protein by a host cell or synthetically, using known techniques.

An example of this embodiment is a KC protein which has the amino acid sequence of a mature KC protein truncated at its carboxy terminus at a position between amino acids about 58 to about 70 of SEQ ID NO: 1. In a preferred embodiment, the descarboxy KC protein consists of amino acid residues 1 to 68 of the mature KC protein [SEQ ID NO: 1], in which the carboxy terminal four amino acid residues of the mature protein are lacking. Similar descarboxy proteins can be constructed with the gro$\alpha$, gro$\beta$ and gro$\gamma$ proteins.

It is anticipated that other desamino and descarboxy chemokine may also exhibit enhanced biological activity as compared to the respective unaltered mature chemokine. Examples of such chemokines include a subfamily chemokines such as IL-8/NAP-1, PF-4, and IP-10, $\beta$ subfamily chemokines such as MCAF/MCP-1, LD-78, PAT464, GOS19-1, ACT-2, PAT744/G26, RANTES, I-309, and the above-described proteins. These proteins are all described in the literature and are known to those of skill in the art.

Moreover, as described in more detail below, modified proteins of this invention include multimeric forms of the modified and/or truncated proteins, e.g., dimers, trimers, tetramers and other aggregated forms. Such multimeric forms can be prepared by synthesis or recombinant expression and can contain chemokines produced by a combination of synthetic and recombinant techniques as detailed below. Multimers may form naturally upon expression or may be constructed into such multiple forms.

It is anticipated that multimeric forms of the modified chemokines of this invention may include multimers of the same modified chemokine. Another multimer of this invention is formed by the aggregation of different modified proteins. Still another multimer of this invention is formed by the aggregation of a modified chemokine of this invention and a known, full-length mature chemokine.

Preferably, a dimer or multimer of the invention would contain at least one of the descarboxy or desamino chemokine proteins of the invention and at least one other chemokine or other protein characterized by having the same type of biological activity. This other protein may be an additional desamino or descarboxy chemokine, or another, known protein.

For example, a desirable dimer of the invention comprises two desamino KC proteins of the invention. Other desirable dimers of the invention are two descarboxy-KC proteins of the invention, a desamino-KC and a descarboxy-KC of the invention, or two desamino gro-$\beta$ proteins of the invention. Alternatively, another dimer of the invention may be a desamino KC protein of the invention or a descarboxy-KC protein of the invention in combination with an unmodified mature KC protein. Similarly, such combinations of dimers may be formed with the descarboxy gro-$\alpha$, gro-$\beta$, gro-$\gamma$, or other chemokines of this invention. For example, a desamino gro-$\beta$ protein of the invention may form a dimer with an unmodified mature gro-$\beta$ protein of the invention. One of skill in the art may obtain other desirable multimers using the modified chemokines of the invention.

The multimers, as well as the other modified proteins of this invention, are characterized by enhanced biological activity in contrast to the known mature proteins. Enhanced biological activity provides a clear advantage for therapeutic use, i.e., that less of the protein therapeutic need be administered to obtain a desired therapeutic result. Such a lower dose may result in lower toxicity and lower cost.

Thus, the present invention provides a method of enhancing the biological activity of a selected chemokine, e.g., KC, gro-$\alpha$, gro-$\beta$, and gro-$\gamma$. This method involves modifying natively or recombinantly produced mature chemokines as described herein. This method can also involve preparing multimeric aggregations thereof. According to another embodiment of this method, the modified proteins or multimers may be synthesized as described below.

Advantageously, this method involves preparing the desamino and descarboxy chemokines of this invention following known techniques. For example, these peptides are prepared by the solid phase technique of Merrifield, *J. Am. Chem. Soc.*, 85:2149 (1964), or solution methods known to the art may be successfully employed. The methods of peptide synthesis generally set forth in J. M. Stewart and J. D. Young, "Solid Phase Peptide Synthesis", Pierce Chemical Company, Rockford, Ill. (1984) or M. Bodansky, Y. A. Klauser and M. A. Ondetti, "Peptide Synthesis", John Wiley & Sons, Inc., New York, N.Y. (1976) may be used to produce the peptides of this invention.

Each amino acid or peptide is suitably protected as known in the peptide art. For example, the $\alpha$-fluoroenylmethyloxycarbonyl group (Fmoc) or t-butoxycarbonyl (t-Boc) group are preferred for protection of the amino group, especially at the $\alpha$-position. A suitably substituted carbobenzoxy group may be used for the $\epsilon$-amino group of lysine and benzyl group for the $\beta$ and $\gamma$ carboxy groups of Asp and Glu respectively. Suitable substitution of the carbobenzoxy protecting group is ortho and/or para substitution with chloro, bromo, nitro or methyl, and is used to modify the reactivity of the protective group. Except for the t-Boc group, the protective groups are, most conveniently, those which are not removed by mild acid treatment. These protective groups are removed by such methods as catalytic hydrogenation, sodium in liquid ammonia or HF treatment as known in the art.

If solid phase synthetic methods are used, the peptide is built up sequentially starting from the carboxy terminus and working toward the amino terminus of the peptide. Solid phase synthesis is begun by covalently attaching the C terminus of a protected amino acid to a suitable resin, such as benzhydrylamine resin (BHA), methylbenzhydrylamine resin (MBHA) or chloromethyl resin (CMR), as is generally set forth in U.S. Pat. No. 4,244,946 or phenyl acid amino methyl resin (PAM). A BHA or MBHA support resin is used if the carboxy terminus of the product peptide is to be a carboxamide. ACMR or PAM resin is generally used if the carboxy terminus of the product peptide is to be a carboxy group, although this may also be used to produce a carboxamide or ester.

The protective group on the $\alpha$-amino group is removed by mild acid treatment (i.e. trifluoroacetic acid). Suitable deprotection, neutralization and coupling cycles known in the art are used to sequentially add amino acids without isolation of the intermediate, until the desired peptide has been formed. The completed peptide may then be deblocked and/or split from the carrying resin in any order.

Treatment of a resin supported peptide with HF or HBr/acetic acid splits the peptide from the resin and produces the carboxy terminal amino acid as a carboxylic acid or carboxamide.

If an ester is desired, the CMR or Pam resin may be treated with an appropriate alcohol, such as methyl, ethyl, propyl, butyl or benzyl alcohol, in the presence of triethylamide to cleave the peptide from the resin and product the ester directly.

Esters of the peptides of this invention may also be prepared by conventional methods from the carboxylic acid precursor. Typically, the carboxylic acid is treated with an alcohol in the presence of an acid catalyst. Alternatively, the carboxylic acid may be converted to an activated acyl intermediate, such as an acid halide, and treated with an alcohol, preferably in the presence of a base.

The preferred method for cleaving a peptide from the support resin is to treat the resin supported peptide with anhydrous HF in the presence of a suitable cation scavenger, such as anisole or dimethoxybenzene. This method simultaneously removes all protecting groups, except a thioalkyl group protecting sulfur, and splits the peptide from the resin. Peptides hydrolyzed in this way from the CMR and Pam resins are carboxylic acids, those split from the BHA resin are obtained as carboxamides.

Modification of the terminal amino group of the peptide is accomplished by alkylation or acylation by methods generally known in the art. These modifications may be carried out upon the amino acid prior to incorporation into the peptide, or upon the peptide after it has been synthesized and the terminal amino group liberated, but before the protecting groups have been removed.

Typically, acylation is carried out upon the free amino group using the acyl halide, anhydride or activated ester, of the corresponding alkyl or aryl acid, in the presence of a tertiary amine. Monoalkylation is carried out most conveniently by reductive alkylation of the amino group with an appropriate aliphatic aldehyde or ketone in the presence of a mild reducing agent, such as a lithium or sodium cyanoborohydride. Dialkylation may be carried out by treating the amino group with an excess of an alkyl halide in the presence of a base.

Solution synthesis of peptides is accomplished using conventional methods used for amide bonds. Typically, a protected t-Boc amino acid which has a free carboxyl group is coupled to a protected amino acid which has a free amino group using a suitable coupling agent, such as N,N'-dicyclohexyl carbodiimide (DCC), optionally in the presence of catalysts such as 1-hydroxybenzotriazole (HOBT) or dimethylamino pyridine (DMAP). Other methods, such as the formation of activated esters, anhydrides or acid halides, of the free carboxyl of a protected t-Boc-amino-acid, and subsequent reaction with the free amine of a protected amino acid, optionally in the presence of a base, are also suitable. For example, a protected Boc-amino acid or peptide is treated in an anhydrous solvent, such as methylene chloride or tetrahydrofuran (THF), in the presence of a base, such as N-methyl morpholine, DMAP (dimethylaminopyridine) or a trialkyl amine, with isobutyl chloroformate to form the "activated anhydride", which is subsequently reacted with the free amine of another protected amino acid or peptide. The peptide formed by these methods may be deprotected selectively, using conventional techniques, at the amino or carboxy terminus and coupled to other peptides or amino acids using similar techniques. After the peptide has been completed, the protecting groups may be removed as hereinbefore described, such as by hydrogenation in the presence of a palladium or platinum catalyst, treatment with sodium in liquid ammonia, hydrofluoric acid or alkali.

If the final peptide, after it has been deprotected, contains a basic group, an acid addition salt may be prepared. Acid addition salts of the peptides are prepared in a standard manner in a suitable solvent from the parent compound and a slight excess of an acid, such as hydrochloric, hydrobromic, sulfuric, phosphoric, acetic, maleic, succinic or methanesulfonic. The acetate salt form is especially useful. If the final peptide contains an acidic group, cationic salts may be prepared. Typically the parent compound is treated with a slight excess of an alkaline reagent, such as a hydroxide, carbonate or alkoxide, containing the appropriate cation. Cations such as $Na^+$, $K^+$, $Ca^{++}$ and $NH_4^+$ are examples of cations present in pharmaceutically acceptable salts. $Na^+$ and $NH_4^+$ are especially preferred.

However, in a preferred method, full-length, mature chemokines are digested with a suitable enzyme to produce the modified proteins of the present invention. Currently, the preferred enzyme is DPP-IV, which is commercially available from Enzyme Products Systems, Inc.

The desamino and descarboxy chemokines of this invention may also be produced by other techniques known to those of skill in the art, for example, genetic engineering techniques. See, e.g., Sambrook et al, in *Molecular Cloning, a Laboratory Manual*, 2nd edition, Cold Spring Harbor Laboratory, Cold Spring Harbor, N.Y. (1989). Systems for cloning and expression of a selected protein in a desired microorganism or cell, including, e.g. *E. coli*, Bacillus, Streptomyces, mammalian, insect, and yeast cells, are known and available from private and public laboratories and depositories and from commercial vendors.

Currently, the most preferred method of producing the descarboxy and desamino chemokines of the invention is through direct recombinant expression of the modified chemokine. For example, the descarboxy or desamino murine KC protein can be recombinantly expressed by inserting its DNA coding sequence into a conventional plasmid expression vector under the control of regulatory sequences capable of directing the replication and expression of the protein in a selected host cell. See, for example, the description in Examples 2 and 3 below.

The recombinant expression of the desamino and/or descarboxy groα, groβ, and groγ can be obtained using analogous techniques. Among the preferred expression systems for these chemokines also includes eukaryotic cells, including insect and yeast cells. However, the most preferred expression system, as with the KC, is a bacterial system. Because these proteins are not believed to be glycosylated, there appears to be no conformational problems associated with translation and expression in bacteria.

The modified chemokines of the invention which are produced in the cell or secreted into the medium can then be purified therefrom using conventional techniques such as cell lysis and gel chromatography.

Desirably, these desamino and descarboxy chemokines of the invention naturally combine, including those synthetically produced in monomeric form, into dimers, trriers, and other aggregates. For example, a monomeric descarboxy-KC protein of the invention may be co-expressed in a selected host cell which has been co-transfected with one or more vectors containing the coding sequences of the modified chemokine of the invention. Alternatively, two or more copies of the monomeric descarboxy-KC protein of the invention may be on a single vector, or incorporated into a chromosome of a host cell. Preferably, this host cell is bacterial or mammalian.

Thus, as another embodiment of the invention, nucleic acid sequence encoding the modified chemokines of the invention may be obtained conventionally or designed by one of skill in the art with knowledge of the amino acid sequences of the chemokine. Such nucleic acid sequences can be designed with preferred codons for the expression system selected, e.g., bacterial, yeast, etc. Similarly, the nucleotide sequences encoding the expression plasmids may be obtained conventionally depending upon the selection of the plasmid and the selection of the modified chemokine protein to be expressed therein. The nucleotide sequences encoding these proteins may also contain an optional initiating Met codon.

In another aspect, the present invention further provides pharmaceutical compositions useful in the treatment of inflammation, fever, viral, fungal, and bacterial infections, cancer, myelopoietic dysfunction, hematopoiesis disorders, and autoimmune diseases. These compositions contain a therapeutically effective amount of a modified chemokine of this invention and an acceptable pharmaceutical carrier. As used herein, the term "pharmaceutical" includes veterinary applications of the invention.

Modified chemokines of the invention for therapeutic use include, without limitation, a desamino KC, a descarboxy-KC, a desamino groβ, gro-α, or gro-γ, or a descarboxy groβ, gro-α, or gro-γ, multimers containing them, and combinations thereof.

The modified chemokines of the invention can be formulated into pharmaceutical compositions and administered in the same manner as described for the mature proteins [see, e.g., International Patent Application, Publication No. WO 90/02762 (Mar. 22, 1990)]. The difference in the preparation and use of the pharmaceutical compositions of this invention is the ability to provide lesser amounts of protein to accomplish the same therapeutic effect for which the mature protein is used. The term "therapeutically effective amount" refers to that amount of a modified chemokine, whether in monomeric or, preferably, multimeric form, which is useful for alleviating a selected condition.

Generally, a desamino or descarboxy chemokine of the invention is administered in an amount between about 0.01 ng/kg body weight to about 1 g/kg and preferably about 0.01 ng/kg to 100 µg/kg per dose. Preferably, these pharmaceutical compositions are administered to human or other mammalian subjects by injection. However, administration may be by any appropriate internal route, and may be repeated as needed, e.g. one to three times daily for between 1 day to about three weeks.

Suitable pharmaceutical carriers are well known to those of skill in the art and may be readily selected. Currently, the preferred carrier is saline. Optionally, the pharmaceutical assays of the invention may contain other active ingredients or be administered in conjunction with other therapeutics. Suitable optional ingredients or other therapeutics include those conventional for treating conditions of this nature, e.g. other anti-inflammatories, diuretics, and immune suppressants, among others. Desirably, these modified chemokines of the invention are particularly well suited for administration in conjunction with colony stimulating factor.

Thus, the invention also provides improved methods of treating inflammation, autoimmune disorders, and conditions characterized by low production and/or differentiation of hematopoietic and/or bone marrow cells. This method involves administering to a selected mammal a pharmaceutical composition of the invention. Preferably, this composition is administered together with or contains a colony stimulating factor. Suitable sources of colony stimulating factor are well known and include, e.g., natural, synthetic and recombinant GM-CSF, M-CSF, G-CSF and IL-3. In another preferred embodiment, a descarboxy or desamino chemokine of the invention can be administered in vivo, and permitted to act in synergy with the natural colony stimulating factors found in a selected patient.

In one preferred embodiment, the descarboxy and desamino chemokines of the invention are particularly well suited for internal use in conjunction with GM-CSF, an approved treatment for such conditions which is unfortunately extremely toxic. The use of a modified chemokine of the invention, such as a desamino gro-β, in combination with CSF, which combination has been observed to have synergy, permits lower doses of CSF to be administered to a patient, resulting in a lower toxicity of the GM-CSF.

In another aspect, the present invention provides antibodies to the modified chemokines of the invention. Such antibodies are characterized by binding preferentially to the modified chemokines of the invention, i.e. they are capable of discriminating against the unmodified or full-length chemokines. These antibodies may be generated using conventional techniques for production of monoclonal [W. D. Huse et al, *Science,* 246:1275–1281 (1989); Kohler and Milstein] or polyclonal antibodies. The antibodies of the invention are anticipated to be useful as diagnostic reagents for measuring levels of hematopoietic synergistic factor (HSF) in a mammal's blood stream.

The present invention further provides a method for monitoring the circulating level and/or efficacy of a selected agent characterized by the ability to induce HSF in a mammal. Such HSF-inducing agents include, without limitation, hematopoiesis-inducing compounds such as those disclosed in co-owned application Ser. No. 07/819, 024, corresponding to issued Canadian patent No. 2,020, 838, and in U.S. Pat. No. 4,987,122.

These peptides are illustrated by the formula (I):

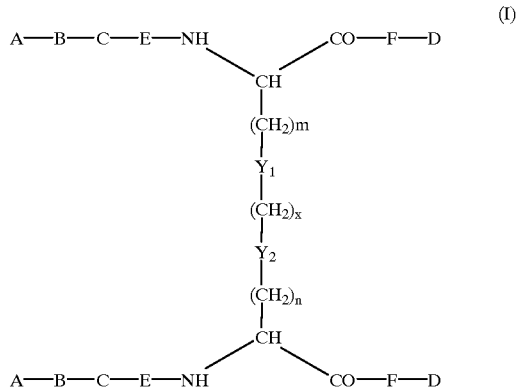

wherein:
$Y_1$ and $Y_2$ are independently $CH_2$ or S;
x is 0, 1, 2, 3, or 4;
m is 0, 1, or 2;
n is 0, 1, or 2;
A is pyroglutamic acid, proline, glutamine, tyrosine, glutamic acid, 2-thiophene carboxylic acid, picolinic acid, cyclohexane carboxylic acid, tetrahydro-2-furoic acid, tetrahydro-3-furoic acid, 2-oxo-4-thiazolidine, cyclopentane, 3-thiophene carboxylic acid, (S)-(+)-5-oxo-2-tetrahydrofuran-carboxylic acid, and pipecolinic acid;
B is serine, glutamic acid, tyrosine or aspartic acid;
C is glutamic acid, tyrosine or aspartic acid;
D is lysine, arginine, tyrosine, N-methylarginine, aspartic acid, ornithine or diaminohexynoic acid; or the carboxyamide, or hydroxy methyl derivative thereof;
E is glutamic acid, aspartic acid, tyrosine or a peptide bond;
F is tyrosine or a peptide bond;
provided that:
when $Y_1$ and $Y_2$ are S, x is 2, 3 or 4 and m and n are 1; or when $Y_1$ and $Y_2$ are $CH_2$, x is 0, 1 or 2 and m and n are 0; or when $Y_1$ is S and $Y_2$ is $CH_2$, x is 0 and n is 1; or when $Y_2$ is S and $Y_1$ is $CH_2$, x is 0 and m is 1; or a pharmaceutically acceptable salt thereof.

Also included in this invention are pharmaceutically acceptable salt complexes of the compounds of this invention. It should be noted in formula (I) that A comprises the terminal amino group of the amino acid residue corresponding to pyroglutamic acid, proline, glutamine, tyrosine or glutamic acid. Similarly, D comprises the terminal carboxyl group of amino acid residue corresponding to lysine, arginine, tyrosine, N-methyl argininet diamino hexynoic acid or the carboxamide or hydroxy methyl derivative thereof.

The abbreviations and symbols commonly used in the art are used herein to describe the peptides. Amino acids are abbreviated by their conventional three-letter designations.

pGlu=pyroglutamic acid
Pic=picolinic acid
Ppc=pipecolinic acid
Ppg=propargyl glycine
Orn=ornithine
p-($NH_2$)Phe=para-aminophenylalanine
Hna=2,6-diamino-4-hexynoic acid

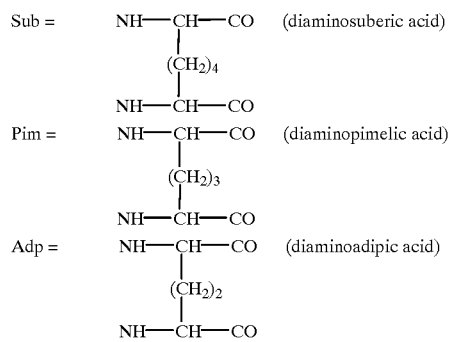

Chc=cyclohexane carboxylic acid
Tfc=tetrahydro-2-furoic acid
Otz=2-oxo-4-thiazolidine
Cpa=cyclopentane
Tpc=3-thiophene carboxylic acid
S-Otf=(S)-(+)-5-oxo-2-tetrahydrofuranecarboxylic acid
t-BOC=tert. butyloxy carbonyl
Bz=benzyl
Cl-Z=p-chloro carbobenzyloxy carbonyl (Z=carbobenzyloxy carbonyl)
DCC=dicylohexyl carbodiimide
DIEA=diisopropylethyl amine
EDC=(N-ethyl-N'-(3-dimethylaminopropyl) carbodiimide
Hna=diaminohexynoic acid
HOBT=hydroxybenzotriazole
NMP=N-methyl-2-pyrrolidinone
N-MeArg=N-methyl arginine
Prc=bis BOC-S,S'=1,3-propanediylcysteine
Etc=bis BOC-S,S'-1,2-ethanediylcysteine
Buc=bis BOC-S,S'-1,4-butanediylcysteine
R-Otf=(R)-(–)-5-oxo-2-tetrahydrofuranecarboxylic acid In accordance with conventional representation, the amino terminus is on the left and the carboxy terminus is on the right. All chiral amino acids may be in the D or L absolute configuration. All optical isomers are contemplated.

The amino terminus may be protected by acylation. Examples of such protecting groups are, t-butoxycarbonyl (t-Boc), $CH_3CO$ and Ar—CO (Ar=benzyl, or phenyl).

The C-terminus may be carboxy as in the case of the natural amino acid or the carboxamide —C(O)$NH_2$ or hydroxymethyl (—$CH_2$—OH).

Preferred compounds are those in which:
A is pyroglutamic acid, picolinic acid, proline, tyrosine, or pipecolinic acid;
B is glutamic acid, serine, aspartic acid or tyrosine;
C is aspartic acid, glutamic acid, tyrosine or lysine;
D is lysine, or the carboxyamide derivative thereof, arginine, N-methylarginine, 2,6-diamino-4-hexynoic acid, aspartic acid or ornithine;
E is a bond;
$Y_1$ and $Y_2$ are $CH_2$;
x is 0 or 2;
m and n are 0.

More preferred are compounds wherein:
A is pyroglutamic acid, proline or picolinic acid;
B is glutamic acid, aspartic and or serine;
C is aspartic acid or glutamic acid;
D is lysine or the carboxyamide derivative thereof;
E is a bond;
$Y_1$ and $Y_2$ are $CH_2$; and
x is 0 or 2 and the chiral amino acids are in the L absolute configuration.

Especially preferred are:
(pGlu-Glu-Asp)$_2$Sub(Lys)$_2$ [SEQ ID NO: 5]
(pGlu-Glu-Asp)$_2$Adp(Lys)$_2$ [SEQ ID NO: 6]
(pGlu-Glu-Glu)$_2$Sub(Lys)$_2$ [SEQ ID NO: 7]
(pGlu-Asp-Asp)$_2$Sub(Lys)$_2$ [SEQ ID NO: 8]
(Pic-Glu-Asp)$_2$Sub(Lys)$_2$ [SEQ ID NO: 9]
(L-Ppc-Glu-Asp)$_2$Sub(Lys)$_2$ [SEQ ID NO: 10]
(pGlu-Ser-Asp)$_2$Sub(Lys)$_2$ [SEQ ID NO: 11]
(pGlu-Ser-Asp)$_2$Adp(Lys)$_2$ [SEQ ID NO: 12]
(pGlu-Ser-Asp)$_2$Adp(Lys-$NH_2$)$_2$ [SEQ ID NO: 13]
(Pic-Ser-Asp)$_2$Adp(Lys)$_2$ [SEQ ID NO: 14]
(Pic-Ser-Asp)$_2$Adp(Lys-$NH_2$)$_2$ [SEQ ID NO: 15]
(pGlu-Glu-Asp)$_2$Adp(Tyr-Lys)$_2$ [SEQ ID NO: 16]
(Pic-Glu-Asp)$_2$Adp(Lys)$_2$ [SEQ ID NO: 17]
(p-Glu-Glu-Asp)$_2$Sub(Lys-$NH_2$)$_2$ [SEQ ID NO: 18]
(Pic-Glu-Asp)$_2$Adp(Lys-$NH_2$)$_2$ [SEQ ID NO: 19]

Of the above-described peptides, the most preferred is (pGlu-Glu-Asp)$_2$-Sub-(Lys)$_2$ [SEQ ID NO: 5]. These peptides may be prepared by the solid phase or solution phase techniques described above.

This method of the invention involves contacting a sample of body fluids from a mammal to which has been previously administered the HSF inducing agent with an antibody of the invention. The preferred body fluids are blood, plasma and serum. However, other suitable samples can be readily determined. The antibody is used to measure the levels of HSF. The circulating HSF levels following administration of the HSF-inducing agent are compared to a base-line level or the circulating HSF levels prior to administration of the HSF-inducing agent. From the measurement of induced HSF levels, the therapeutic efficacy of the selected agent can be determined, and treatment can be monitored and adjusted as necessary.

For example, a monoclonal or polyclonal anti-desaminogroα antibody may desirably be used as a reagent in an assay for detecting the levels of HSF induced by, e.g., (pGlu-Glu-Asp)$_2$-Sub-(Lys)$_2$. Suitable assay formats are well known in the art. Currently, however, the preferred format is an enzyme-linked immunosorbent assay (ELISA).

The antibodies of the invention may be associated with individual labels, and where more than one antibody is employed in a diagnostic method, the labels are desirably interactive to produce a detectable signal. Most desirably, the label is detectable visually, e.g. calorimetrically. Detectable labels for attachment to antibodies useful in the diagnostic assays of this invention may also be easily selected by one skilled in the art of diagnostic assays. Labels detectable visually are preferred for use in clinical applications due to the rapidity of the signal and its easy readability. For calorimetric detection, a variety of enzyme systems have been described in the art which will operate appropriately. Colorimetric enzyme systems include, e.g., horseradish peroxidase (HRP) or alkaline phosphatase (AP). Other proximal enzyme systems are known to those of skill in the art, including hexokinase in conjunction with glucose-6-phosphate dehydrogenase. Also, bioluminescence or chemiluminescence can be detected using, respectively, NAD oxidoreductase with luciferase and substrates NADH and FMN or peroxidase with luminol and substrate peroxide. Other conventional label systems that may be employed include fluorescent compounds, radioactive compounds or elements, or immunoelectrodes. These and other appropriate label systems and methods for coupling them to antibodies or peptides are known to those of skill in the art.

The present invention also provides a diagnostic kit which enables the monitoring of circulating levels of HSF in the blood stream. Such a kit may contain a sufficient amount of at least one modified chemokine of the invention or at least one antibody of the invention and such components as are necessary to practice the assay. Such assays are conventional, and the necessary reagents and other components of such a kit are well known to those of skill in the art.

Also provided by the present inventions are methods of inducing HSF in vivo by administering, e.g., (pGlu-Glu-Asp)$_2$-Sub-(Lys)$_2$ [SEQ ID NO: 5]. In general, this or another selected peptide described herein may be administered to human patients by injection in the dose range of 0.5 ng to 1 mg, preferably 5–500 ng, or orally in the dose range of 50 ng to 5 mg, for example, 0.01 mg to 1 mg per 70 kg body weight per day; if administered by infusion or similar techniques, the dose may be in the range 0.005 ng to 1 mg per 70 kg body weight, for example, about 0.03 ng over six days. It is desirable to produce a concentration of peptide of about $10^{-15}$M to $10^{-5}$M in the extracellular fluid of the patient.

Advantageously, the peptide may be administered as the active ingredient in a pharmaceutical composition or a physiologically compatible salt thereof. The peptide or salt may be in association with a pharmaceutical carrier or excipient. The compositions according to the invention may be presented for example, in a form suitable for oral, nasal, parenteral or rectal administration. Suitable carriers and excipients are well known and can be readily determined by one of skill in the art. Dosage units containing the peptide preferably contain 0.1–100 mg, for example 1–50 mg of the peptide of formula (I) or salt thereof.

The following examples illustrate the preferred methods for preparing the modified and truncated chemokines of the invention. Also provided are comparative examples demonstrating the enhanced bioactivity of these chemokines as compared to the chemokines from which they are derived. Examples 9 through 16 provides are illustrations of how the peptides used in the methods of the invention are synthesized. In these examples, all temperatures are in degrees Centigrade. Amino acid analysis were performed upon a Dionex Autoion 100. Analysis for peptide content is based upon Amino Acid Analysis. FAB mass spectra were performed upon a VG ZAB mass spectrometer using fast atom bombardment. These examples are illustrative only and do not limit the scope of the invention.

EXAMPLE 1

Synthesis of Desamino KC

The procedure used for synthesis of modified murine KC protein, amino acid sequence #5–72 of the mature KC protein of SEQ ID NO: 1, follows.

The KC protein sequence was synthesized using solid-phase methods adapted to a fully automated protein synthesizer (Applied Biosystems Model 430 A). Boc-Lys(Cl-Z)-PAM resin (0.75 g, 0.5 mmol) was charged in a reaction vessel and the target protein was synthesized according to the manufacturer's suggested protocols using 2 mmol of each $N^\alpha$-t-Boc amino acid. Each coupling reaction was carried out twice followed by N-capping with acetic anhydride. Sterically hindered residues were coupled a third time. The following side chain protecting groups were used: benzyl (Thr, Ser); 4-methylbenzyl (Cys); toluenesulfonyl (Arg); 2-chlorobenzyloxycarbonyl (Lys); dinitrophenyl (His); cyclohexyl (Asp, Glu). The coupling yields of certain difficult sequences were monitored by the Kaiser test. After completion of the synthesis the protein-resin was washed with DCM and dried.

A portion of the protein-resin (0.2 g, 0.017 mmol) was treated with DMF-BME-DIEA (75:20:5) for 4×30 min. to deprotect the His residues and, after extensive washing with DMF and DCM, the $N^\alpha$-t-Boc group was removed by treatment with 50% TFA in DCM for 20 min. The protein was further deprotected and cleaved from the resin using HF (5 ml) at −5° C. for one hour in the presence of anisole (0.5 ml), dimethylsulfide (0.5 ml) and p-thiocresole (0.1 g). The HF was evaporated and the protein-resin mixture was washed with ether containing 5% β-mercaptoethanol (BME). The protein was extracted from the resin with 6 M guanidine HCL/0.1 M HOAc (30 ml). A portion of the crude protein (1.75 ml, ~6.6 mg) was first purified on a preparative size exclusion column (Beckman TSK 3000SW) using phosphate buffered saline (PBS) buffer at a flow rate of 2 ml/min, and then on a C-18 Vydac preparative column using acetonitrile-water (0.1% TFA) buffer system at a flow rate of 5 ml/min. 0.36 mg+of pure protein was obtained. Amino acid analysis and fast atom bombardment-mass spectrometry (FABS-MS) confirmed the structure. FAB-MS: [MH+] at mz: 7457.4 a.m.u., where MH+ represents a positively charged mass ion, m/z is mass/charge and a.m.u. is atomic mass units.

| Amino acid analysis | | | | | |
|---|---|---|---|---|---|
| Asp | 4.00 | (4) | Val | 5.53 | (6) |
| Thr | 3.69 | (4) | Met | 2.44 | (2) |
| Ser | 2.19 | (2) | Ile | 3.18 | (4) |
| Glu | 8.45 | (10) | Leu | 8.01 | (9) |
| Gly | 4.09 | (4) | Pro | 4.02 | (5) |
| Ala | 4.64 | (4) | Arg | 2.09 | (2) |
| His | 1.99 | (2) | Lys | 6.96 | (7) |

Chemically synthesized and native purified full-length KC are both inactive as synergistic factors. Chemically synthesized desamino KC prepared according to this invention is a potent synergistic factor.

EXAMPLE 2

Plasmid Construction for Expression of Murine Desamino KC

A partial cDNA clone encoding full-length murine KC was obtained from the American Type Culture Collection in Rockville, Md. (ATCC No. 37591). A 422 bp TfiI-HincII fragment (bp 125–553) was isolated from this cDNA clone. (All base pair and amino acid numbers refer to the sequence available in Genbank®, accession number J04596.)

A linker comprising bp 74–124 was synthesized with a TfiI overhang at the 3' end and a HindIII overhang at the 5' end using conventional technology. An NdeI site was incorporated at the 5' end to generate a Met codon in-frame with the KC product.

The linker and KC fragment were ligated to pUC18 [ATCC 15752-B1] which had been cut with HindIII and HincII, to generate pMKC. pMKC encodes the entire mature KC gene product (aa 25–96) with the addition of an N-terminal Met.

All E. coli expression of KC and its derivatives was done using plasmid pEA191kn [SmithKline Beecham]. pEA191kn is a derivative of pSKF301 [Shatzman et al, "Expression Using Vectors with Phage λ Regulatory Sequences" in Current Protocols in Molecular Biology, ed. F. A. Ausubel et al, pp. 16.3.1–16.3.11 (1990)] created by 1) removing a portion of the Amp resistance gene and replacing it with a kanamycin resistance gene and 2) inserting the λrexB gene, which was engineered to remove endogenous NdeI sites, upstream of the $P_L$ promoter.

For expression of the full-length mature KC (with the addition of an N-terminal Met) an NdeI-SspI fragment encoding amino acids 25-termination codon with the addition of an N-terminal Met was isolated from pMKC and subcloned into pEA181kn which had been cut with NdeI and HpaI. The resulting clone was designated pEA1/mkc19(wt).

To generate the desamino form of KC, a 322 bp PstI-SspI fragment (bp 112–434) was isolated from pMKC (described above). A linker comprising bp 86–111 was synthesized with a PstI compatible overhang at the 3' end and an NcoI overhang at the 5' end. An NdeI site was incorporated in the 5' end to provide an N-terminal Met in frame with the KC gene product. The fragment and linker were ligated to pEA181kn, cut with NcoI and HpaI. The resulting clone, in which the desamino KC gene is fused to the NS1 gene product, was designated pEA1-NS1/mkc21(−4). To delete the NS1 portion of the fusion, pEA1-NS1/mkc21(−4) was cut with NdeI and religated. The resulting clone was designated pEA/mkc38(−4).

pEA/mkc18(wt) and pEA/mkc39(−4) have been induced with nalidixic acid to express the full-length (amino acids 25-term with the addition of an N-terminal Met) and the desamino (amino acids 29-term with N-terminal Met), respectively. For induction, E. coli AR120 cells [SmithKline Beecham] transformed with the plasmids construct were grown at 37° C. in a gyrotory shaker at 250–300 rpm until $AD_{650}$=0.4–0.6. One one-thousandth of the volume of 60 mg/mL nalidixic acid (made up in 1 N NaOH) was added to give a final concentration of 60 µg/mL. Cultures were grown for 4–5 hours and then harvested. Cells were lysed and crude lysates tested for hematopoietic synergistic factor (HSF) activity as described in Example 8 below.

EXAMPLE 3

Expression of Murine Desamino KC in E. coli

Murine full-length and desamino KC were subcloned to pEA181kn, as described in Example 2 above, where they were expressed under the control of the inducible $P_L$ promoter from bacteriophage λ. Induction of the desamino construct, pEA1/mkc38(−4), with nalidixic acid resulted in production of a 69 amino acid protein (amino acids 29–96 of the mature KC with the addition of a methionine at the amino-terminus). The desamino KC product is soluble and shows synergistic activity when assayed as crude bacterial lysate in the hematopoietic synergistic activity assay described below in Example 8. The 73 amino acid protein produced by nalidixic acid induction of pEA1/mkc18(wt) is also soluble, but showed no synergistic activity unless digested with DPP IV to produce the truncated form of the protein.

The desamino-KC combined with GM-CSF (20 U) resulted in approximately 40–50 colonies of cells, which translated to an activity of approximately $10^{14}$ U.

EXAMPLE 4

Synthesis of Descarboxy-KC

The native full-length and desamino KC forms were purified from murine fibroblastic cell line, C6 [SmithKline Beecham] supernatants by Heparin-agarose affinity chromatography with subsequent reverse phase high performance liquid chromatography (HPLC).

To prepare descarboxy-KC, native full length KC purified as described above, was digested with carboxypeptidase Y to form descarboxy-KC which is theoretically amino acid 1 to 68 of the full length KC [SEQ ID NO: 1]. In contrast to native, full-length KC, this descarboxy-KC is active as a synergistic factor.

EXAMPLE 5

Preparation of Desamino-gro-β

Recombinant, full-length gro-β, which can optionally be obtained from commercial sources, was digested with DPP IV enzyme [Enzyme Product Systems, Inc.] to form desamino gro-β, which spans amino acid 5 to 68 of the full length human gro-β [SEQ ID NO: 3].

Full-length groβ shows no synergistic activity in the hematopoietic synergistic activity assay (0 Units/mg). Digestion of the lysate with DPP IV to produce the truncated form of the protein, results in the appearance of signficant levels of synergistic activity in the lysate; specifically this activity is about $10^8$ Units in the assay of Example 8 when digested for a short-term only. Even higher activities are anticipated with increased duration of digestion.

EXAMPLE 6

Plasmid Construction for Expression of Human Desamino GROβ

In the following description, all amino acid and base pair numbers for human gro β refer to the sequence as obtained in Genbank, accession number M57731. A gene encoding the full-length mature human groβ protein (amino acids 34–106, bp 172–393, with the addition of an N-terminal methionine corresponding to SEQ ID NO: 3) was synthesized and subcloned to pCR2000 [SmithKline Beecham]. The resulting clone was designated pHgroβ. 5' NdeI and 3' HpaI sites were included in the synthesized gene to simplify subsequent subcloning.

For *E. coli* expression, the NdeI-HpaI fragment encoding the entire mature protein (with the addition of an N-terminal Met) was subcloned into pEA181Kn, described above, which had been cut with NdeI and HpaI. The resulting clone was designated pEA1/hgroβ5(wt). This clone can be induced with nalidixic acid as described above to produce a 74 amino acid product corresponding to the full-length mature groβ protein (with the added N-terminal Met).

Figure 6:
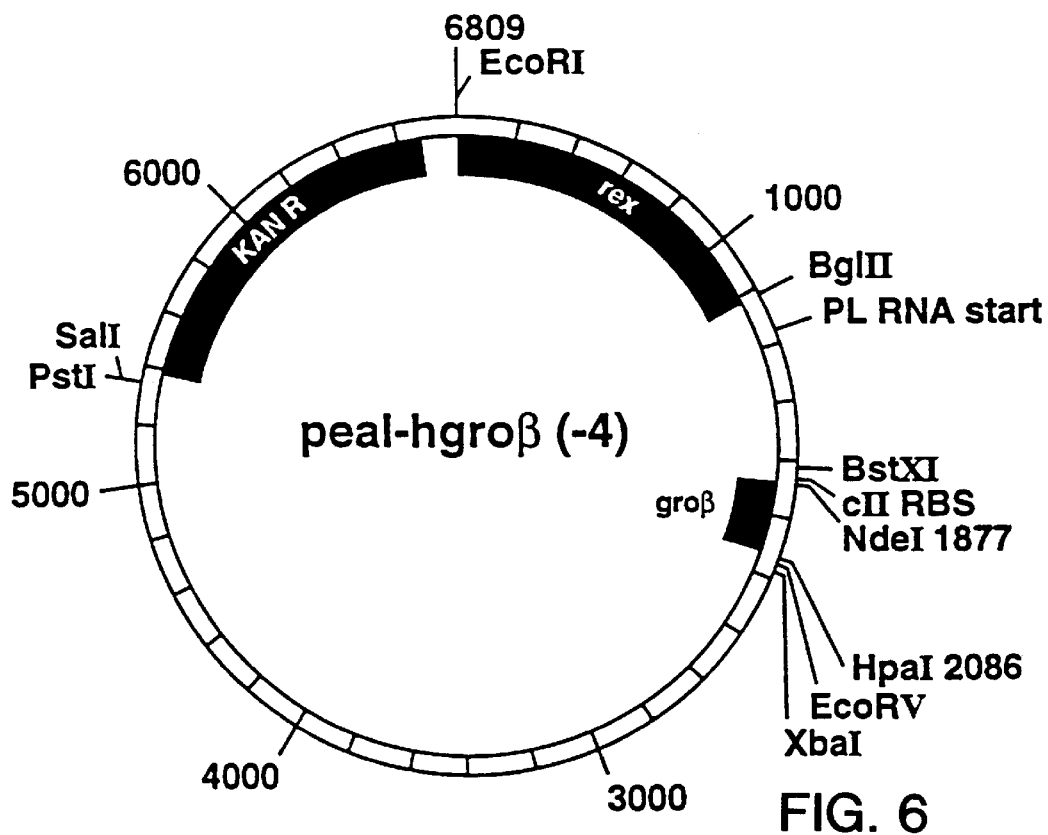
FIG. 6 is a DNA map of the plasmid pea1-hgroβ(−4), which is described below in Example 6.

The desamino form of human groβ was constructed as follows. A 176 bp PstI-HpaI fragment was isolated from pHgroβ and ligated with an NdeI-PstI linker (encoding amino acids 39–49, with the addition of an N-terminal methionine) into NdeI/HpaI cut pEA181kn. The resulting clone is designated pEA1-Hgroβ(-4). FIG. 6 is a DNA map of this plasmid.

pEA1-hgroβ(-4) was induced with nalidixic acid as described above to produce a 70 amino acid groβ protein which is truncated at the amino terminus of the active protein by 4 amino acids (aa 39–106 with the addition of an N-terminal Met).

EXAMPLE 7

Expression of Human Desamino gro-β in *E. coli*

The human groβ (MIP2α) gene was synthesized and subcloned to *E. coli* expression vector pEA181kn, described in Example 6 above, where it is expressed under the control of the inducible $P_L$ promoter derived from bacteriophage λ. Induction with nalidixic acid resulted in the production of a 74 amino acid protein (amino acids 35-termination codon with the addition of an N-terminal methionine).

This recombinant groβ (amino acids 5–73 of SEQ ID NO: 3) was found to have an activity of about $10^{14}$ Units in the assay of Example 8.

EXAMPLE 8

Hematopoietic Synergistic Factor Activity Assay

All modified chemokines are screened in the following conventional assay to determine whether or not the modified chemokine is characterized by synergistic activity with colony stimulating factor (CSF), i.e. the combination of the chemokine and the colony stimulating factor exceeds the additive effect of the two proteins.

Murine bone marrow cells harvested and suspended in RPMI 1649 with 10% fetal bovine serum (FBS). The bone marrow cells are cultured with suboptimal concentrations of recombinant murine Granulocyte-Macrophage (GM)-CSF (20 U/ml) and dilutions of test compounds in a standard murine CFU-GM soft agar assay. Optionally, G-CSF, M-CSF, and IL-3 (low $O_2$ conditions) can be used as an alternate CSF source. Marrow cells cultured with 20 units of GM-CSF results in the growth of approximately 20–30 colonies of cells (background). As is conventional, 1 Unit (U) is equivalent to approximately 1 colony above background.

For example, desamino-KC combined with GM-CSF (20 U/ml) resulted in approximately 40–50 colonies of cells, which translated to a specific activity of approximately $10^{14}$ U/mg. Synthetic groα (amino acids 5–73) are also characterized by having a specific activity of $10^{14}$ U/mg.

Even when using commercially obtained chemokines, which may contain impurities, the method of the invention results in increased activity. For example the following results were obtained using shortened digestion periods.

| | |
|---|---|
| Commercial Groβ + | $2 \times 10^4$ U |
| DPPIV digestion | $1 \times 10^6$ U |
| Commercial groγ + | $2 \times 10^3$ U |
| DPPIV digestion | $5 \times 10^5$ U |

More dramatic increases in activity are anticipated with increased duration of digestion, and with synthetically produced cytokines.

EXAMPLE 9

Preparation of (p-Glu-Glu-Asp)$_2$-Pim-(Lys)$_2$

[SEQ ID NO: 20]

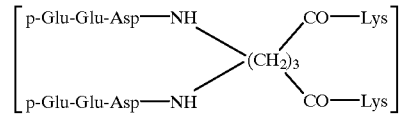

A half gram of t-TOC-Lys(Cl-Z)-0 CH$_2$-Pam Resin (0.63 mmol/gm) was loaded in the reaction vessel of a Beckman 990 B synthesizer. In the deprotection step, the t-Boc group was removed using 40% trifluoroacetic acid (TFA) in methylene chloride (CH$_2$Cl$_2$) and rinsed with CH$_2$Cl$_2$. The trifluoroacetate salt was neutralized by 10% DIEA/CH$_2$Cl$_2$. Two mM (780 mgs) of Di-BOC-2,6-diaminopimelic acid was coupled using 2 mM of DCC and HOBT. The coupling was done in the mixture of 15 ml of CH$_2$Cl$_2$ and 10 ml of DMF at room temperature for two hours. Kaiser's test was used to monitor the coupling. Any remaining free carboxyl groups were amidated twice by using 3 mM (1.65 gms) of H-Lys(Z)-OBz.HCl and 3 mM of DCC and 3 mM of HOBT in 25 ml of CH$_2$Cl$_2$/DMF (15/10).

After two hours of coupling, the resin was washed twice with 15 ml of CH$_2$Cl$_2$, twice with 15 ml of DMF, twice with 15 ml of MeOH/CH$_2$Cl$_2$ (1:1), and finally twice with 15 ml of CH$_2$Cl$_2$. After the deprotection of t-Boc using 40% TFA/CH$_2$Cl$_2$ and the neutralization using 10% DIEA/CH$_2$Cl$_2$, 2 mM (0.646 gm) of Boc-Asp(Bzl) and 2 mM of DCC and 2 mM of HOBT were added and coupled for 2 hours in 25 ml of CH$_2$Cl$_2$/DMF (15/10). The resin was then subjected to a washing step as described earlier. The deprotection step and the neutralization step were repeated before 2 mM (0.674 gm) of Boc-Glu (Bzl), 2 mM DCC and 2 mM of HOBT were coupled in 25 ml of CH$_2$Cl$_2$/DMF (15/10). After washing, deprotection and neutralization steps, 2 mM (0.258 gm) of pGlu, 2 mM of DCC and 2 mM of HOBT were coupled in 25 ml of CH$_2$Cl$_2$/DMF (15/10) for 2 hours before the resin was subjected to a washing step. Completion of the coupling was monitored by Kaiser's test and only single coupling was needed at each step. After the completion of the synthesis the resin was dried and weighed. Yield: 1.2 g.

The peptide resin (1.2 gm) was charged in a cleavage apparatus and cleaved using 10 ml of hydrofluoric acid (HF) and 1 ml anisole at $-15°$ C. for two hours. After removal of HF under vacuum the mixture of resin and peptide was extensively washed with ether and the peptide was extracted in glacial acetic acid (30 ml). Most of the acid was removed from the extracts on a rotavap and the residue was diluted in water and lyophilized. The acetic acid extract had 810 mgs of crude peptide.

The crude peptide (80 mgs), obtained from acetic acid extraction, was further purified using a preparative C-18 column. It was passed through a pre-equilibrated (in 0.1% TFA/$H_2O$) column. The peptide was eluted using a linear gradient of 80% acetonitrile, 20% $H_2O$ and 0.1% TFA.

Three isomers co-eluted (8.52 min). These were separated on a C-18 column using a gradient of 30% (0.1% TFA in $CH_3CN$), 70% (0.1% TFA in $H_2O$) to 80% (0.1% TFA in $CH_3CN$), 20% (0.1% TFA in $H_2O$) over 35 minutes at a flow rate of 1.5 ml/min. The following fractions were eluted:

fraction 1: 18.69 min fraction 2: 19.68 min fraction 3: 22.95 min

Amino acid analysis gave the following results:

| Amino Acid Analysis | Observed |
|---|---|
| Glu | 1.99 |
| Asp | 1.0 |
| Lys | 1.05 |
| Bis amino pimelic acid | N.D. | mass spec = 1157.5 $(M + H)^+$

EXAMPLE 10

Preparation of (pGlu-Glu-Asp)$_2$-Lan-(Lys)$_2$ [SEQ ID NO: 21]

[Lan=Lanthionine(SCH$_2$CH(NH$_2$)COOH)]

A half gram of t-BOC-Lys(Cl-Z)-CH$_2$ PAM (0.63 m. m/g) is charged in the reaction vessel of a Beckman 990 synthesizer. The t-BOC group is removed using 40% TFA in methylene chloride. The trifluoroacetic acid salt is neutralized by 10% DIEA/CH$_2$Cl$_2$. Two mM of Bis BOC lanthionine is coupled using 4 mM of DCC and HOBT in 15 ml of CH$_2$Cl$_2$ and 10 ml of DMF at room temperature. The Kaiser test is used to monitor the coupling. Any free remaining carboxyl groups are amidated using 3 mM of H-Lys (Z)-OBz.HCl; and 3 mM of DCC and HOBT in 25 ml of CH$_2$Cl$_2$/DMF (15/10). After the coupling resin is extensively washed with CH$_2$Cl$_2$, 30% MeOH—CH$_2$Cl$_2$, and CH$_2$Cl$_2$ (25 ml×3), the cycles of deprotection, neutralization and coupling are repeated with the remaining amino acids in the target peptide (Asp, Glu, pGlu). Four mM of each amino acid, DCC and HOBT are used for each coupling. Each coupling is monitored using Kaiser test. After completion of the synthesis, the resin is dried and weighed.

The peptide resin is charged in cleavage apparatus and cleaved using 10 ml of hydrofluoric acid (HF) and one ml of anisole at $-15°$ C. for two hours. After removal of the HF, the resin is extensively washed with ether and the peptide is extracted with glacial acetic acid (30 ml). Most of the acetic acid is removed on a rotavap and the residue is diluted in water and lyophilized. After purification of HPLC, the peptide is obtained.

EXAMPLE 11

Preparation of (pGlu-Glu-Asp)$_2$-Pim-(Arg-CONH$_2$)$_2$ [SEQ ID NO: 22]

A half gram of BOC-Tos Arg-BHA resin (0.5 m. M/g) is charged in the reaction vessel of a Beckman 990 synthesizer. The BOC group is removed using 40% TFA in methylene chloride. The trifluroacetic acid salt is neutralized by 10% DIEA/CH$_2$Cl$_2$. One mM of Bis BOC pimelic acid is coupled using 2 mM of DCC and HOBT in 15 ml of CH$_2$Cl$_2$ and 10 ml of DMF at room temperature. The Kaiser test is used to monitor the coupling. Any free remaining carboxyl groups are amidated using 3 mM of H-Lys (Z)-OBz.HCl; and 3 mM of DCC and HOBT in 25 ml of CH$_2$Cl$_2$/DMF (15/10). After coupling, the resin is extensively washed with CH$_2$Cl$_2$, 30% MeOH—CH$_2$Cl$_2$, and CH$_2$Cl$_2$ (25 ml×3). The cycles of deprotection, neutralization and coupling are repeated with the remaining amino acids in the target peptide (Asp, Glu and p-Glu). 3 mM of amino acid, DCC and HOBT are used for each coupling. Each coupling is monitored using the Kaiser test. After completion of the synthesis, the resin was dried and weighed.

The peptide resin is charged in a cleavage apparatus and cleaved using 10 ml of hydrofluoric acid (HF) and one ml of anisole at $-15°$ C. for two hours. After removal of the HF, the resin is extensively washed with ether and the peptide is extracted with glacial acetic acid (30 ml). Most of the acetic acid is removed on a rotavap and the residue is diluted in water and lyophilized. After purification by HPLC the peptide is obtained.

EXAMPLE 12

Synthesis of Tyrosine Containing Analogs (Tyr-Glu-Asp)$_2$-Sub-(Lys)$_2$ [SEQ ID NO: 23];

(pGlu-Tyr-Glu-Asp)$_2$-Sub-(Lys)$_2$ [SEQ ID NO: 24];

(pGlu-Glu-Tyr-Asp)$_2$-Sub-(Lys)$_2$ [SEQ ID NO: 25];

(pGlu-Glu-Asp-Tyr)$_2$-Sub-(Lys)$_2$ [SEQ ID NO: 26].

Two grams of BOC-Lys(Cl-Z)-0-Resin (Peninsula Labs®, substitution 0.49 mM/g) was charged in a manual shaker vessel. After deprotection and neutralization steps, 2 mM (808 mg) of di-BOC diaminosuberic acid was coupled to the resin using 4 mM (824 mg) of dicyclohexylcarbodiimide (DCC) and 4 mM (612 mg) of 1-hydroxybenzotriazole hydrate (HOBT) in 25 ml of 50% N-methyl-2-pyrrolidinone (NMP) and dichloromethane (DCM). The reaction was allowed to proceed overnight followed by the addition of 10 mM (4.06 g) H-Lys (Z)-OBz.HCl, 10 mM (1.29 g) diisopropylethylamine (DIEA), 10 mM (2.06 g) DCC and 10 mM (1.53 g) HOBT. After two hours, the unreacted amino groups were capped using 10% acetic anhydride in NMP/DCM (1:1). Approximately one third of the resulting BOC-Sub-Lys-resin was transferred to another reaction vessel. The major fraction of the resin is called fraction I, and minor fraction is called fraction II. The standard deprotection, neutralization and coupling cycles were used to couple BOC-Tyr (Br-Z), BOC-Asp(OBz), BOC-Glu(OBz), and p-Glu to the resin in fraction II. Five mM of amino acid, DCC and HOBT were used. Coupling was performed in 2 5 ml NMP/DCM (1/1) and was monitored for completion using the Kaiser test. Five mM of BOC-Asp(OBz) were coupled to the resin in fraction I. One fourth of the resulting BOC-Asp-(OBz)Sub-Lys(Cl-Z) resin was transferred to another vessel (fraction III). The remaining resin is called fraction IV. Standard deprotection, neutralization and coupling cycles were used to couple BOC-Tyr (Br-Z), BOC-Glu(OBz), and p-Glu to resin in fraction III. Five mM of amino acid, DCC and HOBT were used. Coupling was performed in 25 ml NMP/DCM (1/1) and was monitored for completion using Kaiser test. Five mM of BOC-Glu(OBz) were coupled to the resin in the major fraction (fraction IV). One third of this resin was transferred to another vessel and 5 mM of p-Glu were coupled to this fraction (fraction VI) resulting in the synthesis of pGlu-Glu-Asp-Sub-Lys-Resin. Five mM of BOC Tyr(Br-Z) were coupled to the major fraction (fraction V) and the resin was further split in halves. One half of the resin was saved as is and to the other half of the resin (fraction VII) 5 mM of p-Glu were coupled resulting in the synthesis of p-Glu-Tyr-Glu-Asp-Sub-Lys-Resin. These resin peptides were deprotected and cleaved using HF/anisole at 0° C. for one hour. The crude peptides (approx. 100 mg) were purified on a C-18 VYDAC 2.5 cm×30 cm preparative column using water/0.1% trifluoroacetic acid (TFA), and acetonitrile/0.01% TFA buffer system.

EXAMPLE 13

Preparation of (pGlu-Glu-Asp)$_2$Prc(Lys)$_2$ [SEQ ID NO: 27]

a. Synthesis of Bis BOC-S,S'-1-3-propanediylcysteine

Three ml of methanol were saturated with dry ammonia and 0.5 g BOC-cysteine in 0.5 ml methanol was added, followed by the addition of 0.35 ml of 1,3 dibromopropane. Ten minutes later, additional 0.5 g of BOC-cysteine in 0.5 ml methanol was added. After 4.5 hours, the solvent was evaporated and the oily residue dissolved in water. The pH of the solution was adjusted to 9, and the solution was extracted with ether. The aqueous layer was acidified to pH 2 and extracted with ethylacetate. The organic layer was dried and evaporated to yield 1.12 g of Bis BOC-S,S-1,3-propanediylcysteine. The amino acid was used without any further purification, FAB/MS M+H=469.

b. Preparation of (pGlu-Glu-Asp)$_2$Prc(Lys)$_2$ [SEQ ID NO: 27]

BOC-Lys resin (0.53 g, substitution 0.63 mM/g) was charged in a manual shaker and after deprotection and neutralization cycles, bis BOC-S,S'-1,3-propanediylcysteine (290 mg, 0.6 mM) was coupled using 1 mM (206 mg) DCC and 1 mM (153 mg) HOBT in 10 ml NMP/DCM (1/1). After two hours, the resin was washed with NMP and DCM and 2 mM (765 mg) of H-Lys (Z)-OBz.HCl was added followed by the addition of 1.5 mM (390 mg) DCC and 1.5 mM (230 mg) of HOBT in 4 ml of NMP/DCM (1/1). After 18 hours, the resin was washed using 20 ml NMP and DCM. Normal deprotection and neutralization and coupling cycles were repeated for the coupling of BOC-Asp(OBz), BOC-Glu (OBz) and p-Glu. One mM of amino acid, DCC and HOBT were used. Coupling was done in 5 ml of NMP/DCM (1/1). Completion of the coupling was monitored using Kaiser's test. The resulting resin peptide (416 mg) was deprotected and cleaved using 0.5 ml anisole and 8 ml of HF at 0° C. for 2 hours. HF was evaporated and the peptide resin mixture was washed with ether and extracted with glacial acetic acid. After lyophilization, 130 mg of the crude peptide was obtained. The crude peptide (61.5 mg) was purified on a C18 VYDAC preparative column using acetonitrile-water (0.1% TFA) buffer system. 16.5 mg of pure peptide was obtained. FAB/MS: M+H 1249.3

| Amino Acid Analysis | |
|---|---|
| Asp | 2.0 (2) |
| Glu | 4.28 (4) |
| Dpc | 1.14 |
| Lys | 1.96 (2) |

EXAMPLE 14

Synthesis of:
((d)-pGlu-Glu-Asp)$_2$-Sub-(Lys)$_2$ [SEQ ID NO: 28]
(pGlu-Glu-Glu)$_2$-Sub-(Lys)$_2$ [SEQ ID NO: 7]
(pGlu-(d)-Glu-Asp)$_2$-Sub-(Lys)$_2$ [SEQ ID NO: 29]
(pGlu-Asp-Asp)$_2$-Sub-(Lys)$_2$ [SEQ ID NO: 8]

A half gram (0.5 g) of t-BOC-Lys (Cl-Z)-0 CH$_2$-Pam Resin (0.63 m mol/gm) was loaded in a manual shaker vessel. In the deprotection step, the BOC group was removed using 40% Trifluoroacetic acid (TFA) in melthylene chloride (CH$_2$Cl$_2$). Trifluoroacetate salt was neutralized by 10% DIEA/CH$_2$Cl$_2$. After the deprotection and neutralization steps, Di-BOC-2,6-diaminosuberic acid (0.16 mM, 66.2 mgs) was coupled using 0.315 mM of DCC and HOBT. The coupling was done in the mixture of 5 ml of CH$_2$Cl$_2$ and 5 ml of DMF at room temperature for four days. Kaiser's test was used to monitor the coupling. The unreacted amino groups were capped using a 10% acetic anhydride/DMF solution. Standard deprotection, neutralization and coupling cycles were then followed and the targeted sequence was assembled. Three mM of amino acid, DCC and HOBT were used. Coupling time was four hours. Completion of the coupling was monitored by Kaiser's test and only single coupling was needed at each step. The peptide resin was loaded in a cleavage apparatus and cleaved using 10 ml of hydrofluoric acid (HF) and 1 ml anisole at −15° C. for two hours. After removal of HF under vacuum, the mixture of resin and peptide was extensively washed with ether and the peptides were extracted in 0.1% TFA and lyophilized. Purification and characterization: The crude peptides were purified using preparative C-18 columns. The column was pre-equlibrated in 99.9% water and 0.1% TFA and the peptide was eluted using a linear gradient of 80% acetonitrile, 20% water and 0.1% TFA. The peptides were analyzed for amino acid composition. The molecular weight was determined usign FAB MS. FAB and amino acid analysis:

FAB MS (M+H 1171.5)
Amino acid analysis: Asp 1.98(2), Glu 4.6(4) and Lys 2(2)
HPLC purity>95%

EXAMPLE 15

Preparation of (Pic-Ser-Asp)$_2$-Adp-(Lys)$_2$ [SEQ ID NO: 14]

a. Synthesis of Boc-Lys(Cl-Z)-Resin

Boc-Lys(Cl-Z) [16.6 g, 40 mmol] was dissolved in 150 ml of 10% H$_2$O in MeOH. The solution was neutralized using 40 ml of 1M CsCO$_3$ solution. The neutralized solution was concentrated using a rotary evaporator. The resulting cesium salt was diluted with DMF and the DMF was removed using a rotary evaporator. This step was repeated two more times. The salt was dried in vacuo for four hours.

The cesium salt of Boc-Lys(Cl-Z) was diluted with 120 ml DMF. To this, was added chloromethyl resin. The reaction mixture was swirled at 40° C. for 48 hours.

The resin was cooled to room temperature and filtered through a fritted funnel and washed sequentially as follows: 500 ml DMF; 500 ml DMF: H₂O (1:1); 500 ml DMF; 500 ml MeOH and 1000 ml CH₂Cl₂. The resin was dried in vacuum. The desired Boc-Lys(Cl-Z)-resin was recovered.

b. Synthesis of Boc-Asp(OBz))₂-Adp-[Lys(Cl-Z)]₂-resin

The Boc-Lys(Cl-Z)-resin was transferred into a reaction vessel and was suspended in CH₂Cl₂.

The Boc protection of the Boc-Lys(Cl-Z) resin was removed by washing the resin with 40 ml 50% TFA in CH₂Cl₂ for 5 minutes followed by another 40 ml of 50% TFA wash for 30 minutes. The resin was then washed three (3) times with 40 ml CH₂Cl₂.

The resulting TFA salt was treated twice with 40 ml 10% DIEA in CH₂Cl₂ for 1 minute, washed once with 40 ml CH₂Cl₂ and once more with 40 ml of 10% DIEA in CH₂Cl₂. The resin was thoroughly washed with CH₂Cl₂ (6×40 ml).

For coupling N,N' di-Boc diaminoadipic acid (Boc-Adp-OH) to the NH2-Lys(Cl-Z)-resin, the resin was suspended in 100 ml methylene chloride (CH₂Cl₂) in a manual shaker vessel. In another 50 ml flask, Boc-Adp-OH and HOBT were dissolved in 5 ml N-methyl pyrrolidone (NMP) and 20 ml CH₂Cl₂. The solution was cooled to 0° C. using an ice bath. To this solution was added DCC and the reaction mixture was stirred at 0° C. for 15 minutes. The resulting precipitates of dicyclihexylurea were filtered off and the pre-formed active ester was added to the NH₂-Lys(2-Cl-Z)-resin suspension. The reaction was monitored using the Kaiser test (Ninhydrin). After 96 hours, the dipeptide-resin was washed with CH₂Cl₂ (3×40 ml), (3×40 ml) and CH₂Cl₂ (6×40 ml). Ninhydrin test after work-up gave a slight blue tint solution compared to the negative control. The resin was then washed once with 10% acetic anhydride in CH₂Cl₂ for 10 minutes and finally with CH₂Cl₂ (6×40 ml).

c. Synthesis of [Boc-Asp(OBz)]₂-Adp-[Lys(Cl-Z)]₂-resin

The TFA deprotection and neutralization steps were repeated to prepare the dipeptide-resin for the Boc-Asp (OBz) coupling. For coupling this amino acid, Boc-Asp (OBz), and HOBT were used. The coupling was complete after 24 hours as indicated by negative ninhydrin test. This tripeptide-resin was also used to make other peptides with different amino acids at position 2 (B).

A half gram of [BOC-Asp(OBz)]₂-Adp-[Lys(Cl-Z)]₂-resin was used for the synthesis of (Pic-Ser-Asp)₂-Adp-(Lys)₂ [SEQ ID NO: 14]. The deprotection, neutralization and coupling cycles were repeated with BOC-Ser(Bz)-OH and Picolinic acid. 1.8 mM of amino acids, DCC and HOBT were used in coupling. The couplings were done in 10 ml DMF/CH₂Cl₂. The peptide-resin was cleaved and crude peptide obtained. The crude peptide was purified on a C-18 VYDAC preparative column, using acetonitrile/water TFA buffer system. Thirteen milligrams of pure peptide were obtained.

FAB MS (M+H 1047.4)

Amino acid analysis: Asp 2.00(2), Ser 1.62(2), Lys 1.81 (2) (Pic and Adp were not analyzed).

HPLC purity>95

EXAMPLE 16

Preparation of (pGlu-Glu-Asp)₂-Sub-(Lys)₂

[SEQ ID NO: 5]

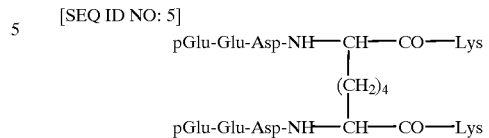

a. Synthesis of BOC-SUB-Lys-(ε-Z)COOBz

Bis-BOC (1,1) diaminosuberic acid (Sub) was synthesized using R. Nutt's method [*J. Org. Chem.*, 45:3078 (1980)].

Two mM of Boc-Sub (808 mg), 4 mM of Lys-(ε-Z)-COOBz.HCl (1.56 g) and 4 mM of HOBT (0.613 g) were dissolved in 10 ml of methylene chloride (CH₂Cl₂) and the solution was chilled to −15° C. using an ice/acetone bath. Four mM (0.692 ml) of diisopropyl ethyl amine (DIEA) were added followed by the addition of 0.772 g (4 mM) water soluble carbodiimide (EDC). After stirring for one hour the mixture was allowed to warm to room temperature. After three hours the methylene chloride was evaporated and the residue was dissolved in 200 ml of ethyl acetate. The solution was washed first with 1N HCl, then 1N NaOH, saturated NaCl solution and water. The washes were repeated three times and each was was about 100 ml. The organic layer was dried over MgSO₄ and evaporated. 1.86 g of BOC-Sub-(ε-Z)Lys-COOBz (79% yield) was obtained and used further without any purification.

b. Synthesis of BOC Asp-(β-OBz)Sub Lys-(ε-Z)-COOBz

BOC-Sub-Lys(ε-Z)-COOBz (1.8 g) was dissolved in 4N HCl-dioxane for a half hour and then evaporated to dryness. The residue was washed with ether and dried overnight. The hydrochloride salt was dissolved in 30 ml of CH₂Cl₂ and BOCAsp-(β-OBz) (1.292 g) was added. The solution was chilled to −15° C. and 0.613 g HOBT, 0.554 ml DIEA and 0.772 g of EDC were added. After stirring for two hours the mixture was allowed to warm up to room temperature. After 18 hours (overnight) the reaction mixture was worked up. CH₂Cl₂ was evaporated and the residue was dissolved in 200 ml of ethyl acetate. The solution was washed with 1N HCl, 1N HaOH, saturated NaCl solution and water (washes were repeated three times and each was was about 100 ml). The organic layer was dried over MgSO₄ and evaporated. BOC-Asp-(β-OBz)-Sub-Lys-(ε-Z)COOBz 1.9 g (yield 73%). This peptide was used without any further purification.

c. Synthesis of BOC-Glu-(γ-OBz) Asp-(β-OBz)Sub-Lys-(ε-Z)COOBz

BOC-(β-OBz) Asp-Sub-(ε-Z) Lys-COOBz, 1.8 g, was dissolved in 15 ml of 4N HCl dioxane. After fifteen minutes the solvent was removed and the residue was washed with ether and dried. The hydrochloride salt was dissolved in 15 ml of N-methyl pyrrolidone (NMP). The solution is chilled to −15° C. and 4 mM (1.338) of BOC-Glu(γ-OBz), 0.204 ml DIEA, 0.772 g EDC and 0.612 g of HOBT was added. The mixture was stirred overnight while gradually warming up to room temperature. The reaction mixture was added to a flask containing one liter of chilled 10% Na₂CO₃ in saturated NaCl solution. The precipitates were filtered, washed with water, and dried under vacuum. BOC-(γ-OBz)Glu-(β-OBz) Asp-Sub-(ε-Z)Lys-COOBz (1.3 g) was obtained and used without any further purification. Yield: 68%.

d. Synthesis of pGlu-(γ-OBz) Glu-(β-OBz) Asp-Sub-(ε-Z) Lys-COOBz

BOC-(γ-OBz) Glu-(β-OBz) Asp-Sub-(ε-Z) Lys-COOBz 1.2 g was dissolved in 15 ml of 4N HCl dioxane. After fifteen minutes, the solvent was removed and the residue was washed with ether and dried. The hydrochloride salt was dissolved in 15 ml of NMP. The solution is chilled to −15° C. and 4 mM (0.516 g) pyro-Glu(p-Glu), 0.106 ml DIEA, 0.772 g EDC and 0.612 g of HOBT were added. The mixture was stirred overnight while gradually warming up to room temperature. The reaction mixture was added to a flask containing one liter of chilled 10% $Na_2CO_3$ in saturated NaCl solution. The precipitates were filtered, washed with water and dried under vacuum. pGlu-(γ-OBz) Glu-(β-OBz) Asp-Sub-(ε-Z) Lys-COOBZ (0.830G) was obtained and used without any further purification. Yield: 69%.

e. Synthesis of pGlu-Glu-Asp-Sub-Lys-COOH pGlu-(γOBz) Glu-(β-OBz) Asp-Sub-(ε-Z) Lys-COOBz (0.200 g) was deprotected using 5 ml HF/1.5 ml anisole at 0° C. HF is removed and the peptide is partitioned between ether and 0.1 N acetic acid. The aqueous layer is washed and lyophilized. pGlu-Glu-Asp-Sub-Lys-COOH 0.089 g is obtained. Twenty mgs of this peptide are purified on C18 prep VYDAC column using isocratic condition (10% acetonitrile, 90% water and 0.1% trifluoroacetic acid, flow rate 5.6 ml/minute). FAB Mass: M+H=1171.4. Amino Acid Analysis: Asp (1.0), Glu (2.19), Lys (1.01), Sub N.D. HPLC: Retention time on C18 VYDAC 0.23×25 mm analytical column 7.01 minute [flow rate 1.5 ml gradient 0% to 80% B A=0.1% TFA in water and B=0.1% TFA in acetonitrile).

EXAMPLE 17

Induction of HSF Using (pGlu-Glu-Asp)$_2$-Sub-(Lys)$_2$ [SEQ ID NO: 5]

Figure 7:
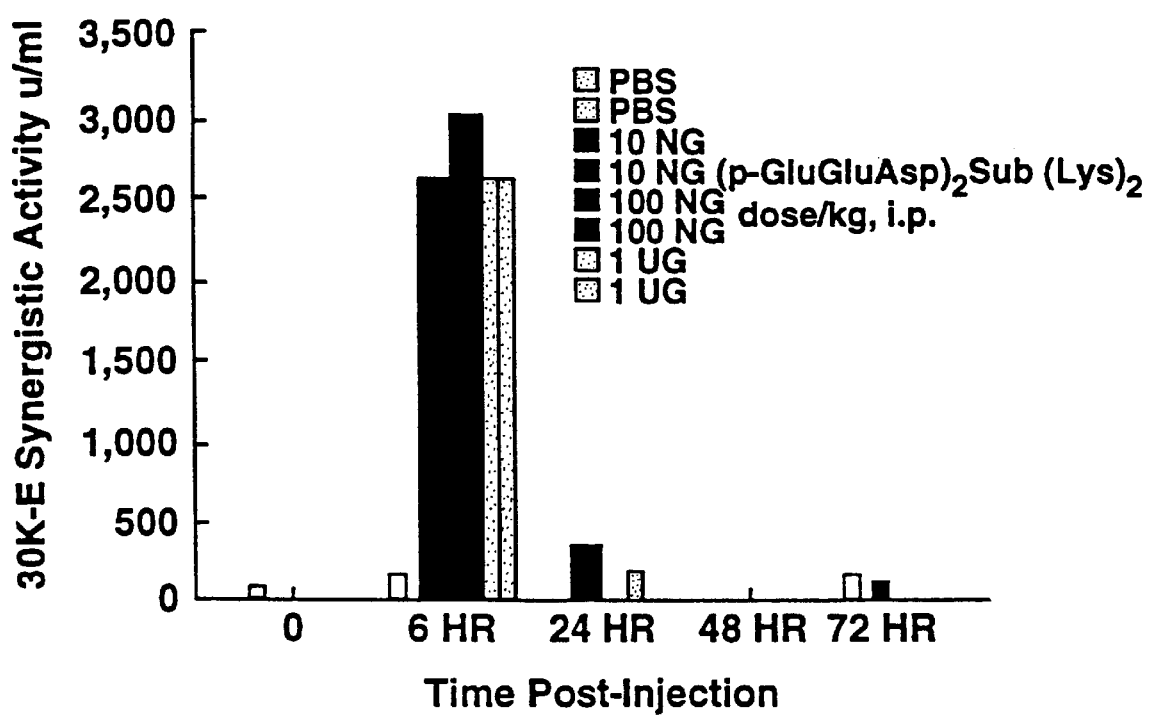
FIG. 7 illustrates the kinetics of HSF induction in vivo, as described in Example 17.
Figure 8:
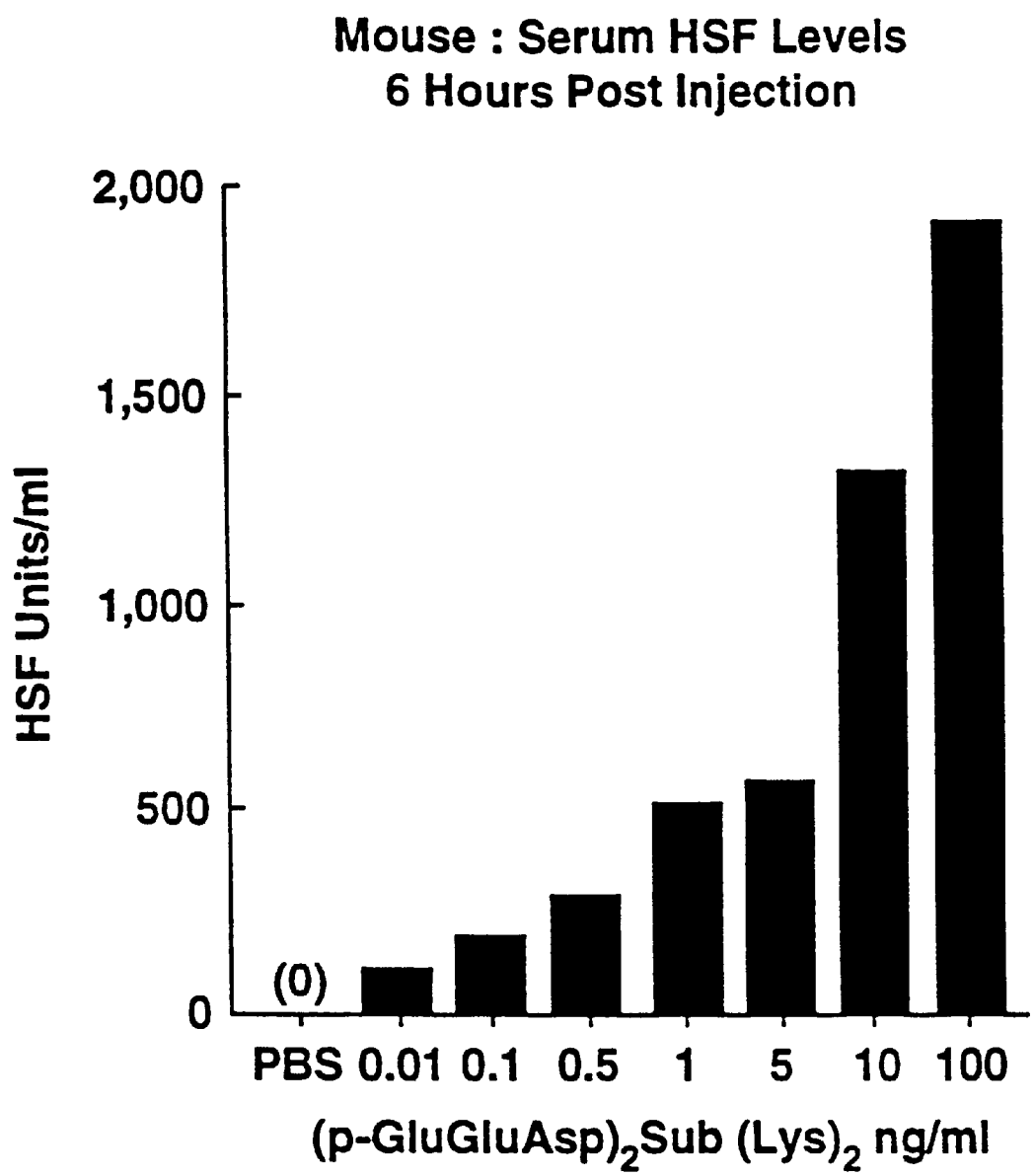
FIG. 8 illustrates the dose-dependent response of serum HSF levels following injection with (pGlu-Glu-Asp)$_2$-Sub-(Lys)$_2$ [SEQ ID NO: 5], as described in Example 17.
Figure 9:
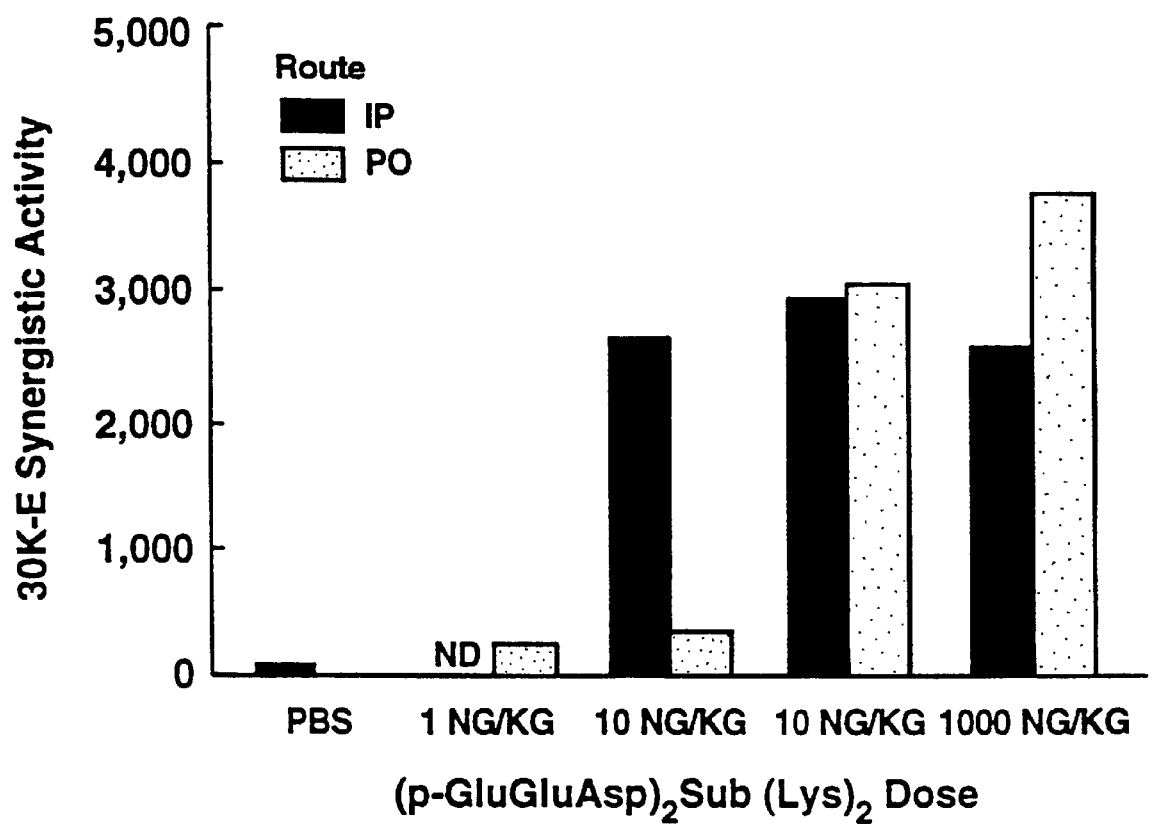
FIG. 9 illustrates dose-dependent response of HSF at 6 hours following intraperitoneal (i.p.) verses oral (p.o.) administration of (pGlu-Glu-Asp)$_2$-Sub-(Lys)$_2$ [SEQ ID NO: 5], as described in Example 17.

C57Black6 [Jackson Laboratories] mice were treated with a single i.p. injection or oral dose of 0.01, 0.1, 0.5, 1, 5, 10 or 100 ng/mL of peptide (pGlu-Glu-Asp)$_2$-Sub-(Lys)$_2$. Phosphate buffered saline (PBS) served as a control. About six hours later, serum from the mice was collected, diluted 1:2 in PBS, then passed through a 30K membrane. The effluent was passed through a 30,000 molecular weight exclusion membrane [Amicon; 30 K-E] was then used in the HSF assay of Example 8. The results are provided in FIGS. 7, 8, and 9. As can be see, none of the PBS treated (control) mice had detectable levels of HSF in their serum. In the treated mice, HSF levels were dose-dependent. These "HSF levels" will be used as surrogate markers for clinical trials.

The crude samples obtained from the HSF assay were purified and sequenced. Analysis revealed that the biologically active peak was the truncated KC of the invention and the inactive peak was full-length KC.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

```
                        SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
          (A) LENGTH: 72 amino acids
          (B) TYPE: amino acid
          (D) TOPOLOGY: unknown (ii) MOLECULE TYPE: protein (xi) SEQUENCE DESCRIPTION: SEQ ID NO:1:

Ala Pro Ile Ala Asn Glu Leu Arg Cys Gln Cys Leu Gln Thr Met Ala
1               5                  10                  15

Gly Ile His Leu Lys Asn Ile Gln Ser Leu Lys Val Leu Pro Ser Gly
            20                  25                  30

Pro His Cys Thr Gln Thr Glu Val Ile Ala Thr Leu Lys Asn Gly Arg
        35                  40                  45

Glu Ala Cys Leu Asp Pro Glu Ala Pro Leu Val Gln Lys Ile Val Gln
    50                  55                  60

Lys Met Leu Lys Gly Val Pro Lys
65                  70

(2) INFORMATION FOR SEQ ID NO:2:

(i) SEQUENCE CHARACTERISTICS:
          (A) LENGTH: 73 amino acids
          (B) TYPE: amino acid
          (D) TOPOLOGY: unknown (ii) MOLECULE TYPE: protein (xi) SEQUENCE DESCRIPTION: SEQ ID NO:2:
```

```
Ala Ser Val Ala Thr Glu Leu Arg Cys Gln Cys Leu Gln Thr Leu Gln
 1               5                  10                  15

Gly Ile His Pro Lys Asn Ile Gln Ser Val Asn Val Lys Ser Pro Gly
                20                  25                  30

Pro His Cys Ala Gln Thr Glu Val Ile Ala Thr Leu Lys Asn Gly Arg
                35                  40                  45

Lys Ala Cys Leu Asn Pro Ala Ser Pro Ile Val Lys Lys Ile Ile Glu
        50                  55                  60

Lys Met Leu Asn Ser Asp Lys Ser Asn
65                  70
```

(2) INFORMATION FOR SEQ ID NO:3:

(i) SEQUENCE CHARACTERISTICS:
        (A) LENGTH: 73 amino acids
        (B) TYPE: amino acid
        (D) TOPOLOGY: unknown (ii) MOLECULE TYPE: protein (xi) SEQUENCE DESCRIPTION: SEQ ID NO:3:

```
Ala Pro Leu Ala Thr Glu Leu Arg Cys Gln Cys Leu Gln Thr Leu Gln
 1               5                  10                  15

Gly Ile His Leu Lys Asn Ile Gln Ser Val Lys Val Lys Ser Pro Gly
                20                  25                  30

Pro His Cys Ala Gln Thr Glu Val Ile Ala Thr Leu Lys Asn Gly Gln
                35                  40                  45

Lys Ala Cys Leu Asn Pro Ala Ser Pro Met Val Lys Lys Ile Ile Glu
        50                  55                  60

Lys Met Leu Lys Asn Gly Lys Ser Asn
65                  70
```

(2) INFORMATION FOR SEQ ID NO:4:

(i) SEQUENCE CHARACTERISTICS:
        (A) LENGTH: 73 amino acids
        (B) TYPE: amino acid
        (D) TOPOLOGY: unknown (ii) MOLECULE TYPE: protein (xi) SEQUENCE DESCRIPTION: SEQ ID NO:4:

```
Ala Ser Val Val Thr Glu Leu Arg Cys Gln Cys Leu Gln Thr Leu Gln
 1               5                  10                  15

Gly Ile His Leu Lys Asn Ile Gln Ser Val Asn Val Arg Ser Pro Gly
                20                  25                  30

Pro His Cys Ala Gln Thr Glu Val Ile Ala Thr Leu Lys Asn Gly Lys
                35                  40                  45

Lys Ala Cys Leu Asn Pro Ala Ser Pro Met Val Gln Lys Ile Ile Glu
        50                  55                  60

Lys Ile Leu Asn Lys Gly Ser Thr Asn
65                  70
```

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown

```
            (ii) MOLECULE TYPE: peptide (ix) FEATURE:
                 (A) NAME/KEY: Modified-site
                 (B) LOCATION: 3..5
                 (D) OTHER INFORMATION: /note= "Asp bonds to NH, Lys
                     bonds
                     to CO, both NH and CO bond to CH which bonds to
                 (CH2)4 which bonds to mirror image of peptide."

(ix) FEATURE:
                 (A) NAME/KEY: Modified-site
                 (B) LOCATION: 3..5
                 (D) OTHER INFORMATION: /note= "Xaa in position 4 is
                     diaminosuberic acid."

(ix) FEATURE:
                 (A) NAME/KEY: Modified-site
                 (B) LOCATION: 1..2
                 (D) OTHER INFORMATION: /note= "Xaa in position 1 is
                     pyroglutamic acid."

(xi) SEQUENCE DESCRIPTION: SEQ ID NO:5:

Xaa Glu Asp Xaa Lys
1               5

(2) INFORMATION FOR SEQ ID NO:6:

(i) SEQUENCE CHARACTERISTICS:
                 (A) LENGTH: 5 amino acids
                 (B) TYPE: amino acid
                 (D) TOPOLOGY: unknown (ii) MOLECULE TYPE: protein (ix) FEATURE:
                 (A) NAME/KEY: Modified-site
                 (B) LOCATION: 1..2
                 (D) OTHER INFORMATION: /note= "Xaa in position 1 is
                     pyroglutamic acid."

(ix) FEATURE:
                 (A) NAME/KEY: Modified-site
                 (B) LOCATION: 3..5
                 (D) OTHER INFORMATION: /note= "Asp bonds to NH, Lys
                     bonds
                     to CO, both NH and CO bond to CH which bonds to
                 (CH2)2 which bonds to mirror image of peptide."

(ix) FEATURE:
                 (A) NAME/KEY: Modified-site
                 (B) LOCATION: 3..5
                 (D) OTHER INFORMATION: /note= "Xaa in position 4 is
                     diaminoadipic acid."

(xi) SEQUENCE DESCRIPTION: SEQ ID NO:6:

Xaa Glu Asp Xaa Lys
1               5

(2) INFORMATION FOR SEQ ID NO:7:

(i) SEQUENCE CHARACTERISTICS:
                 (A) LENGTH: 5 amino acids
                 (B) TYPE: amino acid
                 (C) STRANDEDNESS: unknown
                 (D) TOPOLOGY: unknown (ii) MOLECULE TYPE: peptide (ix) FEATURE:
                 (A) NAME/KEY: Modified-site
                 (B) LOCATION: 3..5
                 (D) OTHER INFORMATION: /note= "Glu bonds to NH, Lys
                     bonds
                     to CO, both NH and CO bond to CH which bonds to
```

```
        (CH2)4 which bonds to mirror image of peptide."

(ix) FEATURE:
        (A) NAME/KEY: Modified-site
        (B) LOCATION: 3..5
        (D) OTHER INFORMATION: /note= "Xaa in position 4 is
            diaminosuberic acid."

(ix) FEATURE:
        (A) NAME/KEY: Modified-site
        (B) LOCATION: 1..2
        (D) OTHER INFORMATION: /note= "Xaa in position 1 is
            pyroglutamic acid"

(xi) SEQUENCE DESCRIPTION: SEQ ID NO:7:

Xaa Glu Glu Xaa Lys
1               5

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 3..5
        (D) OTHER INFORMATION: /note= "Asp bonds to NH, Lys
            bonds
            to CO, both NH and CO bond to CH which bonds
        (CH2)4 which bonds to mirror image peptide."

(ix) FEATURE:
        (A) NAME/KEY: Modified-site
        (B) LOCATION: 3..5
        (D) OTHER INFORMATION: /note= "Xaa in position 4 is
            diaminosuberic acid."

(ix) FEATURE:
        (A) NAME/KEY: Modified-site
        (B) LOCATION: 1..2
        (D) OTHER INFORMATION: /note= "Xaa in position 1 is
            pyroglutamic acid."

(xi) SEQUENCE DESCRIPTION: SEQ ID NO:8:

Xaa Asp Asp Xaa Lys
1               5

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..3
        (D) OTHER INFORMATION: /note= "Xaa in position 1 is
            picolinic acid (Pic)."

(ix) FEATURE:
        (A) NAME/KEY: Modified-site
        (B) LOCATION: 3..5
        (D) OTHER INFORMATION: /note= "Asp bonds to NH, Lys
            bonds
            to CO, both NH and CO bond to CH which bonds to
        (CH2)4 which bonds to mirror image peptide."
```

```
    (ix) FEATURE:
          (A) NAME/KEY: Modified-site
          (B) LOCATION: 3..5
          (D) OTHER INFORMATION: /note= "Xaa in position 4 is
              diaminosuberic acid."

(xi) SEQUENCE DESCRIPTION: SEQ ID NO:9:

Xaa Glu Asp Xaa Lys
1               5

(2) INFORMATION FOR SEQ ID NO:10:

(i) SEQUENCE CHARACTERISTICS:
          (A) LENGTH: 5 amino acids
          (B) TYPE: amino acid
          (C) STRANDEDNESS: unknown
          (D) TOPOLOGY: unknown (ii) MOLECULE TYPE: peptide (ix) FEATURE:
          (A) NAME/KEY: Modified-site
          (B) LOCATION: 1..3
          (D) OTHER INFORMATION: /note= "Xaa in position 1 is
              L-pipecolinic acid (L-Ppc)."

(ix) FEATURE:
          (A) NAME/KEY: Modified-site
          (B) LOCATION: 3..5
          (D) OTHER INFORMATION: /note= "Asp bonds to NH, Lys
              bonds
                to CO, both NH and CO bond to CH which bonds to
          (CH2)4 which bonds to mirror image peptide."

(ix) FEATURE:
          (A) NAME/KEY: Modified-site
          (B) LOCATION: 3..5
          (D) OTHER INFORMATION: /note= "Xaa in position 4 is
              diaminosuberic acid."

(xi) SEQUENCE DESCRIPTION: SEQ ID NO:10:

Xaa Glu Asp Xaa Lys
1               5

(2) INFORMATION FOR SEQ ID NO:11:

(i) SEQUENCE CHARACTERISTICS:
          (A) LENGTH: 5 amino acids
          (B) TYPE: amino acid
          (C) STRANDEDNESS: unknown
          (D) TOPOLOGY: unknown (ii) MOLECULE TYPE: peptide (ix) FEATURE:
          (A) NAME/KEY: Modified-site
          (B) LOCATION: 3..5
          (D) OTHER INFORMATION: /note= "Asp bonds to NH, Lys
              bonds
                to CO, both NH and CO bond to CH which bonds to
          (CH2)4 which bonds to mirror image peptide."

(ix) FEATURE:
          (A) NAME/KEY: Modified-site
          (B) LOCATION: 3..5
          (D) OTHER INFORMATION: /note= "Xaa in position 4 is
              diaminosuberic acid."

(ix) FEATURE:
          (A) NAME/KEY: Modified-site
          (B) LOCATION: 1..2
          (D) OTHER INFORMATION: /note= "Xaa in position 1 is
              pyroglutamic acid."
```

(xi) SEQUENCE DESCRIPTION: SEQ ID NO:11:

Xaa Ser Asp Xaa Lys
1               5

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 3..5
        (D) OTHER INFORMATION: /note= "Asp bonds to NH Lys
            bonds
            to CO, both NH and CO bond to CH which bonds to
        (CH2)2 which bonds to mirror image peptide."

(ix) FEATURE:
        (A) NAME/KEY: Modified-site
        (B) LOCATION: 3..5
        (D) OTHER INFORMATION: /note= "Xaa in position 4 is
            diaminoadipic acid."

(ix) FEATURE:
        (A) NAME/KEY: Modified-site
        (B) LOCATION: 1..2
        (D) OTHER INFORMATION: /note= "Xaa in position 1 is
            pyroglutamic acid."

(xi) SEQUENCE DESCRIPTION: SEQ ID NO:12:

Xaa Ser Asp Xaa Lys
1               5

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 3..5
        (D) OTHER INFORMATION: /note= "Asp bonds to NH,
            position 5
            Xaa bonds to CO, both NH & CO bond to CH which
            bonds to (CH2)2 which bonds to identical
            peptide."

(ix) FEATURE:
        (A) NAME/KEY: Modified-site
        (B) LOCATION: 3..5
        (D) OTHER INFORMATION: /note= "Xaa in position 4 is
            diaminoadipic acid."

(ix) FEATURE:
        (A) NAME/KEY: Modified-site
        (B) LOCATION: 3..5
        (D) OTHER INFORMATION: /note= "Xaa in position 5 is
            Lys-NH2."

(ix) FEATURE:
        (A) NAME/KEY: Modified-site
        (B) LOCATION: 1..2
        (D) OTHER INFORMATION: /note= "Xaa in position 1 is
            pyroglutamic acid."

(xi) SEQUENCE DESCRIPTION: SEQ ID NO:13:

Xaa Ser Asp Xaa Xaa
1               5

(2) INFORMATION FOR SEQ ID NO:14:

(i) SEQUENCE CHARACTERISTICS:
            (A) LENGTH: 5 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Modified-site
            (B) LOCATION: 1..3
            (D) OTHER INFORMATION: /note= "Xaa in position 1 is
                picolinic acid (Pic)."

(ix) FEATURE:
            (A) NAME/KEY: Modified-site
            (B) LOCATION: 3..5
            (D) OTHER INFORMATION: /note= "Asp bonds to NH, Lys
                bonds
                to CO, both NH and CO bond to CH which bonds to
            (CH2)2 which bonds to mirror image peptide."

(ix) FEATURE:
            (A) NAME/KEY: Modified-site
            (B) LOCATION: 3..5
            (D) OTHER INFORMATION: /note= "Xaa in position 4 is
                diaminoadipic acid."

(xi) SEQUENCE DESCRIPTION: SEQ ID NO:14:

Xaa Ser Asp Xaa Lys
1               5

(2) INFORMATION FOR SEQ ID NO:15:

(i) SEQUENCE CHARACTERISTICS:
            (A) LENGTH: 5 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Modified-site
            (B) LOCATION: 1..3
            (D) OTHER INFORMATION: /note= "Xaa in position 1 is
                picolinic acid (Pic)."

(ix) FEATURE:
            (A) NAME/KEY: Modified-site
            (B) LOCATION: 3..5
            (D) OTHER INFORMATION: /note= "Asp bonds to NH,
                position 5
                Xaa bonds to CO, both NH & CO bond to CH which
                bonds to (CH2)2 which bonds to identical
                peptide."

(ix) FEATURE:
            (A) NAME/KEY: Modified-site
            (B) LOCATION: 3..5
            (D) OTHER INFORMATION: /note= "Xaa in position 5 is
                Lys-NH2."

(ix) FEATURE:
            (A) NAME/KEY: Modified-site
            (B) LOCATION: 3..5
            (D) OTHER INFORMATION: /note= "Xaa in position 4 is
                diaminoadipic acid."

(xi) SEQUENCE DESCRIPTION: SEQ ID NO:15:

Xaa Ser Asp Xaa Xaa
1               5

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 3..5
        (D) OTHER INFORMATION: /note= "Asp bonds to NH, Tyr
            bonds
            to CO, both NH and CO bond to CH which bonds to
        (CH2)2 which bonds to mirror image peptide."

(ix) FEATURE:
        (A) NAME/KEY: Modified-site
        (B) LOCATION: 3..5
        (D) OTHER INFORMATION: /note= "Xaa in position 4 is
            diaminoadipic acid."

(ix) FEATURE:
        (A) NAME/KEY: Modified-site
        (B) LOCATION: 1..2
        (D) OTHER INFORMATION: /note= "Xaa in position 1 is
            pyroglutamic acid."

(xi) SEQUENCE DESCRIPTION: SEQ ID NO:16:

Xaa Glu Asp Xaa Tyr Lys
1               5

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..3
        (D) OTHER INFORMATION: /note= "Xaa in position 1 is
            picolinic acid (Pic)."

(ix) FEATURE:
        (A) NAME/KEY: Modified-site
        (B) LOCATION: 3..5
        (D) OTHER INFORMATION: /note= "Asp bonds to NH, Lys
            bonds
            to CO, both NH and CO bond to CH which bonds to
        (CH2)2 which bonds to mirror image peptide."

(ix) FEATURE:
        (A) NAME/KEY: Modified-site
        (B) LOCATION: 3..5
        (D) OTHER INFORMATION: /note= "Xaa in position 4 is
            diaminoadipic acid."

(xi) SEQUENCE DESCRIPTION: SEQ ID NO:17:

Xaa Glu Asp Xaa Lys
1               5

(2) INFORMATION FOR SEQ ID NO:18:

(i) SEQUENCE CHARACTERISTICS:
    (A) LENGTH: 5 amino acids
    (B) TYPE: amino acid
    (C) STRANDEDNESS: unknown
    (D) TOPOLOGY: unknown (ii) MOLECULE TYPE: peptide (ix) FEATURE:
    (A) NAME/KEY: Modified-site
    (B) LOCATION: 3..5
    (D) OTHER INFORMATION: /note= "Asp bonds to NH,
        position 5
        Xaa bonds to CO, both NH & CO bond to CH which
        bonds to (CH2)4 which bonds to identical
        peptide."

(ix) FEATURE:
    (A) NAME/KEY: Modified-site
    (B) LOCATION: 3..5
    (D) OTHER INFORMATION: /note= "Xaa in position 4 is
        diaminosuberic acid."

(ix) FEATURE:
    (A) NAME/KEY: Modified-site
    (B) LOCATION: 3..5
    (D) OTHER INFORMATION: /note= "Xaa in position 5 is
        Lys-NH2."

(ix) FEATURE:
    (A) NAME/KEY: Modified-site
    (B) LOCATION: 1..2
    (D) OTHER INFORMATION: /note= "Xaa in position 1 is
        pyroglutamic acid."

(xi) SEQUENCE DESCRIPTION: SEQ ID NO:18:

Xaa Glu Asp Xaa Xaa
1               5

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..3
        (D) OTHER INFORMATION: /note= "Xaa in position 1 is
            picolinic acid (Pic)."

(ix) FEATURE:
        (A) NAME/KEY: Modified-site
        (B) LOCATION: 3..5
        (D) OTHER INFORMATION: /note= "Asp bonds to NH,
            position 5
            Xaa bonds to CO, both NH & CO bond to CH which
            bonds to (CH2)2 which bonds to identical
            peptide."

(ix) FEATURE:
        (A) NAME/KEY: Modified-site
        (B) LOCATION: 3..5
        (D) OTHER INFORMATION: /note= "Xaa in position 5 is
            Lys-NH2."

(ix) FEATURE:
        (A) NAME/KEY: Modified-site
        (B) LOCATION: 3..5
        (D) OTHER INFORMATION: /note= "Xaa in position 4 is
            diaminoadipic acid."

(xi) SEQUENCE DESCRIPTION: SEQ ID NO:19:

Xaa Glu Asp Xaa Xaa
1               5

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 3..5
        (D) OTHER INFORMATION: /note= "Asp is bound to NH and
            Lys
            is bound to CO, NH and CO are bound to (CH2)3
            which is bound to a mirror image of this
            peptide."

(ix) FEATURE:
        (A) NAME/KEY: Modified-site
        (B) LOCATION: 3..5
        (D) OTHER INFORMATION: /note= "Xaa in position 4 is
            diaminopimelic acid."

(ix) FEATURE:
        (A) NAME/KEY: Modified-site
        (B) LOCATION: 1..2
        (D) OTHER INFORMATION: /note= "Xaa in position 1 is
            pyroglutamic acid."

(xi) SEQUENCE DESCRIPTION: SEQ ID NO:20:

Xaa Glu Asp Xaa Lys
1               5

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 3..5
        (D) OTHER INFORMATION: /note= "Xaa in position 4 is
            Lanthionine [SCH2CH(NH2)COOH] which acts as a
            bridge linking a mirror image peptide."

(ix) FEATURE:
        (A) NAME/KEY: Modified-site
        (B) LOCATION: 1..2
        (D) OTHER INFORMATION: /note= "Xaa in position 1 is
            pyroglutamic acid."

(xi) SEQUENCE DESCRIPTION: SEQ ID NO:21:

Xaa Glu Asp Xaa Lys
1               5

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
            (A) NAME/KEY: Modified-site
            (B) LOCATION: 3..5
            (D) OTHER INFORMATION: /note= "Xaa in position 4 is
                diaminopimelic acid."

(ix) FEATURE:
            (A) NAME/KEY: Modified-site
            (B) LOCATION: 3..5
            (D) OTHER INFORMATION: /note= "Asp is bound to NH and
                position 5 Xaa is bound to CO, NH & CO are bound
                to (CH2)3 which is bound to mirror image
                peptide."

(ix) FEATURE:
            (A) NAME/KEY: Modified-site
            (B) LOCATION: 3..5
            (D) OTHER INFORMATION: /note= "Xaa in position 5 is
                Arg-CONH2"

(ix) FEATURE:
            (A) NAME/KEY: Modified-site
            (B) LOCATION: 1..2
            (D) OTHER INFORMATION: /note= "Xaa in position 1 is
                pyroglutamic acid."

(xi) SEQUENCE DESCRIPTION: SEQ ID NO:22:

Xaa Glu Asp Xaa Xaa
1               5

(2) INFORMATION FOR SEQ ID NO:23:

(i) SEQUENCE CHARACTERISTICS:
            (A) LENGTH: 5 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Modified-site
            (B) LOCATION: 3..5
            (D) OTHER INFORMATION: /note= "Asp bonds to NH, Lys
                bonds
                to CO, both NH and CO bond to CH which bonds to
            (CH2)4 which bonds to mirror image peptide."

(ix) FEATURE:
            (A) NAME/KEY: Modified-site
            (B) LOCATION: 3..5
            (D) OTHER INFORMATION: /note= "Xaa is diaminosuberic
                acid."

(xi) SEQUENCE DESCRIPTION: SEQ ID NO:23:

Tyr Glu Asp Xaa Lys
1               5

(2) INFORMATION FOR SEQ ID NO:24:

(i) SEQUENCE CHARACTERISTICS:
            (A) LENGTH: 6 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Modified-site
            (B) LOCATION: 4..6
            (D) OTHER INFORMATION: /note= "Asp bonds to NH, Lys

```
                    bonds
                    to CO, both NH and CO bond to CH which is bond
                    to
                 (CH2)4 which bonds to a mirror image peptide."

(ix) FEATURE:
           (A) NAME/KEY: Modified-site
           (B) LOCATION: 4..6
           (D) OTHER INFORMATION: /note= "Xaa in position 5 is
                diaminosuberic acid."

(ix) FEATURE:
           (A) NAME/KEY: Modified-site
           (B) LOCATION: 1..2
           (D) OTHER INFORMATION: /note= "Xaa in position 1 is
                pyroglutamic acid."

(xi) SEQUENCE DESCRIPTION: SEQ ID NO:24:

Xaa Tyr Glu Asp Xaa Lys
1               5

(2) INFORMATION FOR SEQ ID NO:25:

(i) SEQUENCE CHARACTERISTICS:
           (A) LENGTH: 6 amino acids
           (B) TYPE: amino acid
           (C) STRANDEDNESS: unknown
           (D) TOPOLOGY: unknown (ii) MOLECULE TYPE: peptide (ix) FEATURE:
          (A) NAME/KEY: Modified-site
          (B) LOCATION: 4..6
          (D) OTHER INFORMATION: /note= "Asp bonds to NH, Lys
                bonds
                to CO, both NH and CO bond to CH which is bond
                to
             (CH2)4 which bonds to mirror image peptide."

(ix) FEATURE:
          (A) NAME/KEY: Modified-site
          (B) LOCATION: 4..6
          (D) OTHER INFORMATION: /note= "Xaa in position 5 is
                diaminosuberic acid."

(ix) FEATURE:
          (A) NAME/KEY: Modified-site
          (B) LOCATION: 1..2
          (D) OTHER INFORMATION: /note= "Xaa in position 1 is
                pyroglutamic acid."

(xi) SEQUENCE DESCRIPTION: SEQ ID NO:25:

Xaa Glu Tyr Asp Xaa Lys
1               5

(2) INFORMATION FOR SEQ ID NO:26:

(i) SEQUENCE CHARACTERISTICS:
           (A) LENGTH: 6 amino acids
           (B) TYPE: amino acid
           (C) STRANDEDNESS: unknown
           (D) TOPOLOGY: unknown (ii) MOLECULE TYPE: peptide (ix) FEATURE:
          (A) NAME/KEY: Modified-site
          (B) LOCATION: 4..6
          (D) OTHER INFORMATION: /note= "Tyr bonds to NH, Lys
                bonds
                to CO, both NH and CO bond to CH which bonds to
             (CH2)4 which bonds to mirror image peptide."

(ix) FEATURE:
```

(A) NAME/KEY: Modified-site
(B) LOCATION: 4..6
(D) OTHER INFORMATION: /note= "Xaa in position 5 is
    diaminosuberic acid."

(ix) FEATURE:
(A) NAME/KEY: Modified-site
(B) LOCATION: 1..2
(D) OTHER INFORMATION: /note= "Xaa in position 1 is
    pyroglutamic acid."

(xi) SEQUENCE DESCRIPTION: SEQ ID NO:26:

Xaa Glu Asp Tyr Xaa Lys
1               5

(2) INFORMATION FOR SEQ ID NO:27:

(i) SEQUENCE CHARACTERISTICS:
    (A) LENGTH: 5 amino acids
    (B) TYPE: amino acid
    (C) STRANDEDNESS: unknown
    (D) TOPOLOGY: unknown (ii) MOLECULE TYPE: peptide (ix) FEATURE:
    (A) NAME/KEY: Modified-site
    (B) LOCATION: 3..5
    (D) OTHER INFORMATION: /note= "Xaa in position 4 is bis
        BOC-S,S'-1,3-propanediylcysteine (Prc) which
        acts
        as a bridge linking a mirror image peptide."

(ix) FEATURE:
    (A) NAME/KEY: Modified-site
    (B) LOCATION: 1..2
    (D) OTHER INFORMATION: /note= "Xaa in position 1 is
        pyroglutamic acid."

(xi) SEQUENCE DESCRIPTION: SEQ ID NO:27:

Xaa Glu Asp Xaa Lys
1             5

(2) INFORMATION FOR SEQ ID NO:28:

(i) SEQUENCE CHARACTERISTICS:
    (A) LENGTH: 5 amino acids
    (B) TYPE: amino acid
    (C) STRANDEDNESS: unknown
    (D) TOPOLOGY: unknown (ii) MOLECULE TYPE: peptide (ix) FEATURE:
    (A) NAME/KEY: Modified-site
    (B) LOCATION: 1..3
    (D) OTHER INFORMATION: /note= "Xaa in position 1 is the
        d-form of pyroglutamic acid."

(ix) FEATURE:
    (A) NAME/KEY: Modified-site
    (B) LOCATION: 3..5
    (D) OTHER INFORMATION: /note= "Asp bonds to NH, Lys
        bonds
        to CO, both NH and CO bond to CH which bonds to
    (CH2)4 which bonds to mirror image peptide."

(ix) FEATURE:
    (A) NAME/KEY: Modified-site
    (B) LOCATION: 3..5
    (D) OTHER INFORMATION: /note= "Xaa in position 4 is
        diaminosuberic acid."

(xi) SEQUENCE DESCRIPTION: SEQ ID NO:28:

```
-continued

Xaa Glu Asp Xaa Lys
1               5

(2) INFORMATION FOR SEQ ID NO:29:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..3
        (D) OTHER INFORMATION: /note= "Glu is in the d-form."

(ix) FEATURE:
        (A) NAME/KEY: Modified-site
        (B) LOCATION: 3..5
        (D) OTHER INFORMATION: /note= "Asp bonds to NH, Lys
            bonds
            to CO, both NH and CO bond to CH which bonds to
        (CH2)4 which bonds to mirror image peptide."

(ix) FEATURE:
        (A) NAME/KEY: Modified-site
        (B) LOCATION: 3..5
        (D) OTHER INFORMATION: /note= "Xaa in position 4 is
            diaminosuberic acid."

(ix) FEATURE:
        (A) NAME/KEY: Modified-site
        (B) LOCATION: 1..2
        (D) OTHER INFORMATION: /note= "Xaa in position 1 is
            pyroglutamic acid."

(xi) SEQUENCE DESCRIPTION: SEQ ID NO:29:

Xaa Glu Asp Xaa Lys
1               5
```

What is claimed is:

1. A modified chemokine, characterized by the truncation of from 2 to 8 amino acids from the amino terminus of the corresponding mature chemokine wherein the mature chemokine is selected from the group consisting of KC, gro-β, gro-γ, and gro-α, consisting of the amino acid sequence shown in SEQ ID NO: 1, SEQ ID NO: 3, SEQ ID NO: 4, or SEQ ID NO: 2, respectively;

and wherein the modified chemokine has at least a log higher biological activity than the corresponding mature chemokine.

2. The modified chemokine according to claim 1 comprising the amino acid sequence of the mature KC protein having an amino terminal truncation of from 2 to 8 amino acid residues from SEQ ID NO: 1.

3. The modified chemokine according to claim 2 consisting of amino acids 5–72 of SEQ ID NO: 1.

4. The modified chemokine according to claim 1 comprising the amino acid sequence of the mature gro-β protein having an amino terminal truncation of from 2 to 8 amino acid residues from SEQ ID NO: 3.

5. The modified chemokine according to claim 1 comprising the amino acid sequence of mature gro-α protein having an amino terminal truncation of from 2 to 8 amino acid residues from SEQ ID NO: 2.

6. The modified chemokine according to claim 5 consisting of amino acids 5 to 73 of SEQ ID NO: 2.

7. The modified chemokine according to claim 1 comprising the amino acid sequence of mature gro-γ protein having an amino terminal truncation of from 2 to 8 amino acid residues from SEQ ID NO: 4.

8. The modified chemokine according to claim 7 consisting of amino acids 5 to 73 of SEQ ID NO: 4.

9. A method of stimulating the growth and/or differentiation of bone marrow cells in a mammal comprising: administering to said mammal a modified chemokine according to claim 1.

10. A method of stimulating maturation of hematopoietic precursor cells in a mammal comprising administering to said mammal a modified chemokine according to claim 1.

11. A method of stimulating the growth and/or differentiation of bone marrow cells in a mammal comprising administering to said mammal a modified chemokine according to claim 1 and a colony stimulating factor.

12. A method of stimulating the growth and/or differentiation of bone marrow cells in a mammal comprising administering to said mammal a mixture of an amount of G-CSF and an amount of a modified chemokine according to claim 1, wherein said mixture elicits a synergistic effect relative to the combination of the effects that said amounts of G-CSF and modified chemokine elicit individually.

13. The modified chemokine consisting of amino acids 5 to 73 of SEQ ID NO: 3.

14. A method of stimulating the growth and/or differentiation of bone marrow cells in a mammal comprising administering to said mammal a mixture of a modified chemokine according to claim 13 and a colony stimulating factor.

15. A multimeric protein which comprises an association of
- (a) one or more modified chemokines, characterized by the truncation of from 2 to 8 amino acids from the amino terminus of the corresponding mature chemokines,
    wherein each mature chemokine is selected from the group consisting of KC, gro-β, gro-γ, and gro-α, consisting of the amino acid sequence shown in SEQ ID NO: 1, SEQ ID NO: 3, SEQ ID NO: 4, or SEQ ID NO: 2, respectively;
    and wherein each modified chemokine has at least a log greater biological activity than the corresponding mature chemokine; and
- (b) a mature chemokine selected from the group consisting of KC, gro-β, gro-γ, and gro-α, wherein the mature chemokine has the amino acid sequence shown in SEQ ID NO: 1, SEQ ID NO: 3, SEQ ID NO: 4, or SEQ ID NO: 2, respectively.

16. The protein according to claim 15 comprising multiple copies of the same modified chemokine.

17. The protein according to claim 15 comprising at least two different modified chemokines.

18. A pharmaceutical composition comprising a suitable pharmaceutical carrier and
- (a) a modified chemokine characterized by the truncation of from 2 to 8 amino acids from the amino terminus of the corresponding mature chemokine,
    wherein the mature chemokine is selected from the group consisting of KC, gro-β, gro-γ, and gro-α, consisting of the amino acid sequence shown in SEQ ID NO: 1, SEQ ID NO: 3, SEQ ID NO: 4, or SEQ ID NO: 2, respectively;
    and wherein the modified chemokine has at least a log higher biological activity than the corresponding mature chemokine; or
- (b) a multimeric protein comprising a modified chemokine according to (a) in association with a second modified chemokine according to (a) or with a mature KC, gro-β, gro-γ, or gro-α chemokine having the amino acid sequence shown in SEQ ID NO: 1, SEQ ID NO: 3, SEQ ID NO: 4, or SEQ ID NO: 2, respectively.

19. A method for treating an inflammatory condition comprising administering to a mammalian subject characterized by said condition an effective amount of a pharmaceutical composition of claim 18.

20. A nucleic acid molecule which upon translation affords a modified chemokine characterized by the truncation of from 2 to 8 amino acids from the amino terminus of the corresponding mature chemokine,
    wherein the mature chemokine is selected from the group consisting of KC, gro-β, gro-γ, and gro-α, consisting of the amino acid sequence shown in SEQ ID NO: 1, SEQ ID NO: 3, SEQ ID NO: 4, or SEQ ID NO: 2, respectively;
    and wherein the modified chemokine has at least a log higher biological activity than the corresponding mature chemokine.

21. A plasmid comprising the nucleic acid sequence of a molecule according to claim 20 under the control of regulatory sequences capable of directing the replication and expression thereof in a host cell.

22. A host cell transfected with a plasmid of claim 21.

23. A method of producing a modified chemokine comprising culturing a host cell of claim 22 under conditions suitable to effect expression of the modified chemokine-encoding sequence and isolating the modified chemokine from the cell or cell culture.

24. A method of enhancing the biological activity of a mature KC, gro-β, gro-γ, or gro-α chemokine comprising the step of removing from the amino terminus thereof 2 to 8 amino acid residues, wherein the mature chemokine consists of the amino acid sequence shown in SEQ ID NO: 1, SEQ ID NO: 3, SEQ ID NO: 4, or SEQ ID NO: 2, and wherein the resulting truncated chemokine has at least a log higher biological activity than the corresponding mature chemokine.

25. A modified chemokine characterized by the truncation of from 2 to 8 amino acids from the amino terminus of the corresponding mature chemokine,
    wherein the mature chemokine is selected from the group consisting of KC, gro-β, gro-γ, and gro-α,
    wherein the mature chemokine consists of the amino acid sequence shown in SEQ ID NO: 1, SEQ ID NO: 3, SEQ ID NO: 4, or SEQ ID NO: 2, respectively, or is a biologically active variant of KC, gro-β, gro-γ, or gro-α which consists of an amino acid sequence differing from SEQ ID NO: 1, SEQ ID NO: 3, SEQ ID NO: 4, or SEQ ID NO: 2 by the substitution of five or fewer amino acid residues;
    and wherein the modified chemokine has at least a log higher biological activity than the corresponding mature chemokine.

26. A modified chemokine according to claim 25 consisting of amino acids 5 to 73 of SEQ ID NO: 3 or a biologically active variant thereof consisting of a sequence which differs from amino acids 5 to 73 of SEQ ID NO: 3 by the substitution of five or fewer amino acid residues.

27. A method of stimulating the growth and/or differentiation of bone marrow cells in a mammal comprising administering to said mammal a modified chemokine according to claim 25.

28. A method of stimulating the growth and/or differentiation of bone marrow cells in a mammal comprising: administering to said mammal a modified chemokine according to claim 26.

29. A method of stimulating maturation of hematopoietic precursor cells in a mammal comprising administering to said mammal a modified chemokine according to claim 25.

30. A method of stimulating maturation of hematopoietic precursor cells in a mammal comprising administering to said mammal a modified chemokine according to claim 26.

31. A method of stimulating the growth and/or differentiation of bone marrow cells in a mammal comprising administering to said mammal a modified chemokine according to claim 25 and a colony stimulating factor.

32. A method of stimulating the growth and/or differentiation of bone marrow cells in a mammal comprising administering to said mammal a modified chemokine according to claim 26 and a colony stimulating factor.

33. A method of stimulating the growth and/or differentiation of bone marrow cells in a mammal comprising administering to said mammal a mixture of an amount of G-CSF and an amount of a modified chemokine according to claim 25, wherein said mixture elicits a synergistic effect relative to the combination of the effects that said amounts of G-CSF and modified chemokine elicit individually.

34. A method of stimulating the growth and/or differentiation of bone marrow cells in a mammal comprising administering to said mammal a mixture of an amount of G-CSF and an amount of a modified chemokine according to claim 26, wherein said mixture elicits a synergistic effect relative to the combination of the effects that said amounts of G-CSF and modified chemokine elicit individually.

35. A multimeric protein which comprises an association of
(a) one or more modified chemokines characterized by the truncation of from 2 to 8 amino acids from the amino terminus of the corresponding mature chemokines,
wherein each mature chemokine consists of the amino acid sequence shown in SEQ ID NO: 1, SEQ ID NO: 3, SEQ ID NO: 4, or SEQ ID NO: 2, respectively, or is a biologically active variant of KC, gro-β, gro-γ, or gro-α which consists of an amino acid sequence differing from SEQ ID NO: 1, SEQ ID NO: 3, SEQ ID NO: 4, or SEQ ID NO: 2 by the substitution of five or fewer amino acid residues,
and wherein each modified chemokine has at least a log higher biological activity than the corresponding mature chemokine; and
(b) a mature chemokine selected from the group consisting of KC, gro-β, gro-γ, and gro α, wherein the mature chemokine has the amino acid sequence shown in SEQ ID NO: 1, SEQ ID NO: 3, SEQ ID NO: 4, or SEQ ID NO: 2, respectively, or is a biologically active variant of KC, gro-β, gro-γ, or gro-α which consists of an amino acid sequence differing from SEQ ID NO: 1, SEQ ID NO: 3, SEQ ID NO: 4, or SEQ ID NO: 2 by the substitution of five or fewer amino acid residues.

36. A multimeric protein according to claim 35 wherein the modified chemokine of (a) consists of amino acids 5 to 73 of SEQ ID NO: 3 or a biologically active variant thereof consisting of a sequence which differs from amino acids 5 to 73 of SEQ ID NO: 3 by the substitution of five or fewer amino acid residues.

37. A method of stimulating the growth and/or differentiation of bone marrow cells in a mammal comprising administering to said mammal a multimeric protein according to claim 36.

38. A method of stimulating maturation of hematopoietic precursor cells in a mammal comprising administering to said mammal a multimeric protein according to claim 36.

39. A method of stimulating the growth and/or differentiation of bone marrow cells in a mammal comprising administering to said mammal a multimeric protein according to claim 36 and a colony stimulating factor.

40. A method of stimulating the growth and/or differentiation of bone marrow cells in a mammal comprising administering to said mammal a mixture of an amount of G-CSF and an amount of a multimeric protein according to claim 36, wherein said mixture elicits a synergistic effect relative to the combination of the effects that said amounts of G-CSF and multimeric protein elicit individually.

41. A pharmaceutical composition comprising a suitable pharmaceutical carrier and
(a) a modified chemokine characterized by the truncation of from 2 to 8 amino acids from the amino terminus of the corresponding mature chemokine,
wherein the mature chemokine consists of the amino acid sequence shown in SEQ ID NO: 1, SEQ ID NO: 3, SEQ ID NO: 4, or SEQ ID NO: 2, respectively, or is a biologically active variant of KC, gro-β, gro-γ, or gro-α which consists of an amino acid sequence differing from SEQ ID NO: 1, SEQ ID NO: 3, SEQ ID NO: 4, or SEQ ID NO: 2 by the substitution of five or fewer amino acid residues;
and wherein the modified chemokine has at least a log higher biological activity than the corresponding mature chemokine; or (b) a multimeric protein comprising a modified chemokine according to (a) in association with a second modified chemokine according to (a) or with a mature KC, gro-β, gro-γ, or gro-α chemokine or biologically active variant thereof having the amino acid sequence shown in SEQ ID NO: 1, SEQ ID NO: 3, SEQ ID NO: 4, or SEQ ID NO: 2 or an amino acid sequence differing from SEQ ID NO: 1, SEQ ID NO: 3, SEQ ID NO: 4, or SEQ ID NO: 2 by the substitution of five or fewer amino acid residues.

42. A pharmaceutical composition according to claim 41 wherein the modified chemokine of (a) consists of amino acids 5 to 73 of SEQ ID NO: 3 or a biologically active variant thereof consisting of a sequence which differs from amino acids 5 to 73 of SEQ ID NO: 3 by the substitution of five or fewer amino acid residues.

43. A method for treating an inflammatory condition comprising administering to a mammalian subject characterized by said condition an effective amount of a pharmaceutical composition of claim 41.

44. A method for treating an inflammatory condition comprising administering to a mammalian subject characterized by said condition an effective amount of a pharmaceutical composition of claim 42.

45. A nucleic acid molecule which upon translation affords a modified chemokine characterized by the truncation of from 2 to 8 amino acids from the amino terminus of the corresponding mature chemokine,
wherein the mature chemokine consists of the amino acid sequence shown in SEQ ID NO: 1, SEQ ID NO: 3, SEQ ID NO: 4, or SEQ ID NO: 2, respectively, or is a biologically active variant of KC, gro-β, gro-γ, or gro-α which consists of an amino acid sequence differing from SEQ ID NO: 1, SEQ ID NO: 3, SEQ ID NO: 4, or SEQ ID NO: 2 by the substitution of five or fewer amino acid residues;
and wherein the modified chemokine has at least a log higher biological activity than the corresponding mature chemokine.

46. A nucleic acid molecule of claim 45 which upon translation affords a modified chemokine consisting of amino acids 5 to 73 of SEQ ID NO: 3 or a biologically active variant thereof consisting of a sequence which differs from amino acids 5 to 73 of SEQ ID NO: 3 by the substitution of five or fewer amino acid residues.

47. A plasmid comprising the nucleic acid sequence of a molecule according to claim 45 under the control of regulatory sequences capable of directing the replication and expression thereof in a host cell.

48. A plasmid comprising the nucleic acid sequence of a molecule according to claim 46 under the control of regulatory sequences capable of directing the replication and expression thereof in a host cell.

49. A host cell transfected with a plasmid of claim 47.

50. A host cell transfected with a plasmid of claim 48.

51. A method of producing a modified chemokine comprising culturing a host cell of claim 49 under conditions suitable to effect expression of the modified chemokine-encoding sequence and isolating the modified chemokine from the cell or cell culture.

52. A method of producing a modified chemokine comprising culturing a host cell of claim 50 under conditions suitable to effect expression of the modified chemokine-encoding sequence and isolating the modified chemokine from the cell or cell culture.

53. A method of enhancing the biological activity of a KC, gro-β, gro-γ or gro-α chemokine comprising the step of removing from the amino terminus thereof 2 to 8 amino acid residues, wherein the resulting truncated chemokine has at least a log higher biological activity than the corresponding intact chemokine.

54. A method according to claim 53, wherein the resulting truncated chemokine consists of amino acids 5 to 73 of SEQ ID NO: 3 or a biologically active variant thereof consisting of a sequence which differs from amino acids 5 to 73 of SEQ ID NO: 3 by the substitution of five or fewer amino acid residues.

* * * * *